US012352758B2

(12) United States Patent
Wagner

(10) Patent No.: US 12,352,758 B2
(45) Date of Patent: Jul. 8, 2025

(54) QUANTITATIVE BIOMARKERS OF EHV-1 SUSCEPTIBILITY AND PROTECTION

(71) Applicant: CORNELL UNIVERSITY, Ithaca, NY (US)

(72) Inventor: Bettina Wagner, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 1322 days.

(21) Appl. No.: 16/975,589

(22) PCT Filed: Feb. 26, 2019

(86) PCT No.: PCT/US2019/019489
§ 371 (c)(1),
(2) Date: Aug. 25, 2020

(87) PCT Pub. No.: WO2019/165397
PCT Pub. Date: Aug. 29, 2019

(65) Prior Publication Data

US 2020/0408777 A1 Dec. 31, 2020

Related U.S. Application Data

(60) Provisional application No. 62/643,801, filed on Mar. 16, 2018, provisional application No. 62/635,232, filed on Feb. 26, 2018.

(51) Int. Cl.
*G01N 33/68* (2006.01)

(52) U.S. Cl.
CPC ..... *G01N 33/6854* (2013.01); *G01N 33/6866* (2013.01); *G01N 33/6893* (2013.01); *G01N 2333/03* (2013.01); *G01N 2333/521* (2013.01); *G01N 2333/56* (2013.01); *G01N 2333/70596* (2013.01); *G01N 2800/26* (2013.01)

(58) Field of Classification Search
CPC ........... G01N 33/6854; G01N 33/6866; G01N 33/6893; G01N 2333/03; G01N 2333/521; G01N 2333/56; G01N 2333/70596; G01N 2800/26
See application file for complete search history.

(56) References Cited

U.S. PATENT DOCUMENTS

| | | | |
|---|---|---|---|
| 10,101,327 | B2 | 10/2018 | Wagner |
| 2011/0059107 | A1 | 3/2011 | Allison et al. |
| 2011/0236968 | A1 | 9/2011 | De Fougerolles et al. |

FOREIGN PATENT DOCUMENTS

| | | | |
|---|---|---|---|
| WO | 2015/073507 | A1 | 5/2015 |

OTHER PUBLICATIONS

Detournay, O. et al., "Genomic Analysis and mRNA Expression of Equine Type I Interferon Genes", J Interferon Cytokine Res., 33: 746-759 (2013).
Edington, N. et al., "The Role of Endothelial Cell Infection in the Endometrium, Placenta and Foetus of Equid Herpesvirus 1 (EHV-1) Abortions", J. Comp. Pathol. 104:379-87 (1991).
Elia, G. et al., "Detection of equine herpesvirus type 1 by real time PCR", J Virol Meth, 133:70-75 (2006).
Fogle, J. et., "Comparison of lipopolysaccharides and soluble CD14 measurement between clinically endotoxaemic and nonendotoxaemic horses", Equine Veterinary Journal, vol. 49, pp. 155-159 (Mar. 2017, published online May 6, 2016).
Goehring, L.S. et al., Equine herpesvirus type 1-associated myeloencephalopathy in The Netherlands: A four-year retrospective study (1999-2003), J. Vet. Intern. Med, 20:601-607 (2006).
Goodman, L.B. et al., "Immunological Correlates of Vaccination and Infection for Equine Herpesvirus 1", Clinical and Vaccine Immunology, vol. 19, No. 2, pp. 235-241 (Feb. 2012, published online Dec. 28, 2011)).
Henninger, R. W, et al., "Outbreak of neurologic disease caused by equine herpesvirus-1 at a university equestrian center", J Am Vet Med Assoc, 21:157-16 (2007).
Kabithe, E. et al., "Monoclonal antibodies to equine CD14", Vet. Immunol. Immunopathol., 138: 149-153 (2010).
Keggan, A. et al., "Production of seven monoclonal equine immunoglobulins isotyped by multiplex analysis", Veterinary Immunology and Immunopathology, vol. 153, No. 3-4, pp. 187-193 (Jun. 15, 2013, published online Feb. 19, 2013).
Kohn, K.W. et al., "Transmission of EHV-1 in horses with EHV-1 myeloencephalopathy: implications for biosecurity and review", Clin Tech Equine Pract, 5:60-66 (2006).
Kydd, J.H. et al., "The equine immune response to equine herpesvirus-1: The virus and its vaccines", Vet Immunol Immunopathol., 111(1-2):15-30 (May 15, 2006).
Li, L. et al., "Early detection of Mycobacterium avium subsp. paratuberculosis infection in cattle with multiplex-bead based immunoassays", PLoS One, 12(12):e0189783 (Dec. 19, 2017).
Lunn, D.P. et al., "Equine herpesvirus-1 consensus statement", J Vet Intern Med, 23:450-461 (2009).
Perkins, G.A. et al., "Investigation of the prevalence of neurologic equine herpes virus type 1 (EHV-1) in a 23-year retrospective analysis (1984-2007)", Vet Microbiol., 139:375-378 (2009).
Schnabel, C.L. et al., "Deletion of the ORF2 gene of the neuropathogenic equine herpesvirus type 1 strain Ab4 reduces virulence while maintaining strong immunogenicity", BMC Vet Res, 14: 245 (2018).
Soboll Hussey, G. et al., "Evaluation of immune responses following infection of ponies with an EHV-1 ORF1/2 deletion mutant", Vet. Res. 42:23, pp. 1-12 (2011).
Wagner, B. et al., "Monoclonal antibodies to equine interferon-alpha (IFN-alpha): New tools to neutralize IFN activity and to detect secreted IFN-alpha", Vet. Immunol. Immunopathol., 125: 315-325 (2008).

(Continued)

*Primary Examiner* — Changhwa J Cheu
(74) *Attorney, Agent, or Firm* — Scully, Scott, Murphy & Presser, P.C.

(57) ABSTRACT

The present disclosure is directed to novel biomarkers useful for staging EHV-1 infections and immunity status of horses. This disclosure is further directed to methods of determining EHV-1 infection stage and immunity status of horses using the novel biomarkers.

15 Claims, 12 Drawing Sheets

(56) References Cited

OTHER PUBLICATIONS

Wagner, B. et al., “Development of a bead-based multiplex assay for simultaneous quantification of cytokines in horses”, Vet Immunol Immunopathol., 127(3-4):242-248 (Feb. 15, 2009, published online Oct. 18, 2008).
Wagner, B. et al., “Analysis of soluble CD14 and its use as a biomarker in neonatal foals with septicemia and horses with recurrent airway obstruction”, Vet. Immunol. Immunopathol., 155: 124-128 (2013).
Wagner, B. et al., “Antibody and cellular immune responses of naïve mares to repeated vaccination with an inactivated equine herpesvirus vaccine”, Vaccine, 33:5588-5597 (2015).
Wagner, B. et al., “Neonatal immunization with a single IL-4/antigen dose induces increased antibody responses after challenge infection with equine herpesvirus type 1 (EHV-1) at weanling age”, PLOS One, 12(1):e0169072, pp. 1-19 (Jan. 3, 2017).
Wimer, C.L. et al., “Equine herpesvirus type-1 modulates CCL2, CCL3, Ccls, CXCL9, and CXCL 10 chemokine expression”, Vet. Immunol. Immunopathol., vol. 40, No. 3-4, pp. 266-274 (Apr. 15, 2011, published online Jan. 26, 2011).
Wimer, C.L. et al., “The deletion of the ORF1 and ORF71 genes reduces virulence of the neuropathogenic EHV-1 strain Ab4 without compromising host immunity in horses”, Plos One, 13(11):e0206679, pp. 1-25 (Nov. 15, 2018).
International Search Report dated May 13, 2019 together with the Written Opinion received in International Application No. PCT/US2019/019489.

A

B

QUANTITATIVE BIOMARKERS OF EHV-1 SUSCEPTIBILITY AND PROTECTION

CROSS REFERENCE TO RELATED APPLICATION

This application claims the benefit of priority from U.S. Provisional Application No. 62/635,232, filed Feb. 26, 2018, and from U.S. Provisional Application No. 62/643,801, filed Mar. 16, 2018, the entire contents of which are incorporated herein by reference.

STATEMENT REGARDING FEDERALLY SPONSORED RESEARCH OR DEVELOPMENT

This invention was made with government support under Grant No. 2015-67015-23091 awarded by the USDA National Institute of Food and Agriculture. The government has certain rights in the invention.

BACKGROUND

Of all viral infections in horses, Equine herpesvirus 1 ("EHV-1") is among the most costly because of the abortions, neonatal mortality, respiratory and neurological diseases (e.g. herpesvirus myeloencephalopathy, EHM) it causes in horses. EHV-1 is transmitted from horse to horse during close contact via respiratory secretions. The virus initially infects the epithelium of the upper respiratory tract. Subsequently, it spreads through the underlying connective tissue to the regional lymphoid tissues, and next establishes cell-associated viremia in leukocytes (Patel J R et al., *Arch. Virol.,* 1982; 74:41-51; Kydd J H et al., *Equine Vet. J.,* 1994; 26:466-9; Kydd J H et al., *Equine Vet. J.,* 1994; 26:470-3; Vandekerckhove A P et al., *Vet. Microbiol.,* 2011; 152:21-8). Infected animals develop antibodies against several antigens of the virus including the envelop glycoproteins gC, gD and gB.

EHV-1 frequently causes disease outbreaks in horse populations including severe neurological outbreaks of equine herpesvirus myeloencephalopathy (EHM) or abortions (Kydd et al., *Vet Immunol Immunopathol.,* 2006; 111:15-30; Lunn et al, *J Vet Intern Med,* 2009; 23:450-461; Perkins et al 2009). In the past 20 years, the increased incidence of morbidity and mortality due to the neurologic manifestation has prompted increased biosecurity (Henninger et al 2007, Kohn et al 2006, Perkins et al., *Vet Microbiol.* 2009; 139: 375-378). During neurological outbreaks, horses are typically quarantined for several weeks. Through lost training and competing time, treatment costs, quarantine, abortion, and death of severely affected horses, EHV-1 has great medical and economic impact (Goehring et al., *J. Vet. Intern. Med.,* 2006; 20:601-607; Lunn et al., *J Vet Intern Med,* 2009; 23:450-461).

Currently, EHV-1 outbreaks are diagnosed by PCR detecting pathogen DNA in the nasal secretion of infected horses. Although PCR is a sensitive technique, it does not take into account the stage of EHV-1 infection or EHV-1 immunity. PCR also does not distinguish infectious virus from inactivated virus-particles (e.g. by neutralizing antibodies), or viral DNA (e.g. dead opsonized virus in macrophages). The latter two mechanisms (i.e. inactivating virus particles by neutralizing antibodies and killing viruses by opsonization of the virus in macrophages) are intact in immune horses and prevent nasal viral shedding and the spread of EHV-1 from horse to horse. Consequently, all horses on a property with an outbreak are quarantined for several weeks based on PCR results and independent of infection stage and immunity status. Fully immune horses do not shed virus or develop disease but current diagnostic methods are not designed to distinguish them from the susceptible group of horses that will develop disease and spread the infection.

Currently, EHV vaccinations are administered every six months for competition horses in order to prevent EHV-1 outbreaks. The racing horse industry has similar requirements for vaccinating horses. However, there is no rational research supporting these EHV vaccination requirements which could lead to possible unnecessary or inefficient vaccination schemes.

SUMMARY OF THE DISCLOSURE

The present disclosure provides a management tool to make informed management decisions during EHV-1 and EHM outbreaks, thereby reducing the time of quarantine needed for immune horses, identifying horses during early infection stages that can undergo treatment to prevent fatal outcomes, and reducing overall costs of these outbreaks and shortening quarantine based on the presence of biomarkers of immunity. The methods and tools of the present disclosure can be applied to horses as well as members of Equidae family such as donkeys and zebras.

The present disclosure also provides a tool to evaluate whether horses are immune against or susceptible for EHV-1 and to make informed decisions if EHV vaccination is required or not needed. This disclosure allows for EHV vaccination management in healthy horses and in the absence of EHV-1/EHM outbreak situations. The disclosed methods and kits provide a tool to optimize immunity against EHV-1 in the individual horse, and thereby in the horse population, with the goal to prevent and/or reduce future EHV-1/EHM outbreaks.

More particularly, the present disclosure identifies biomarkers useful for differentiating among horses that are susceptible or immune to EHV-1 infection, or are undergoing an EHV-1 infection; and for differentiating between horses at an early stage of infection and horses at a late stage of infection. The biomarkers of the present disclosure can be detected from a biological sample such as, for example, nasal secretions (an intranasal sample), serum or plasma (a blood sample).

In one aspect, this disclosure provides a method comprising detecting, in an intranasal sample from a horse, equine herpes virus type 1 (EHV-1) specific immunoglobulin G1 (IgG1) and EHV-1 specific immunoglobulin G4/7 (IgG4/7). In some embodiments, the EHV-1 specific IgG1 and the EHV-1 specific IgG4/7 are both directed against a same glycoprotein of EHV-1. In some embodiments, the method further comprises determining whether the horse is susceptible or immune to EHV-1 infection, or is undergoing an infection. In a specific embodiment, a horse is determined to be susceptible to EHV-1 infection or at an early stage of EHV-1 infection if the levels of the EHV-1 specific IgG1 and the EHV-1 specific IgG4/7 are both below respective threshold levels; the horse is determined to be at a late stage of EHV-1 infection if the levels of the EHV-1 specific IgG1 and the EHV-1 specific IgG4/7 are both above respective threshold levels; and the horse is determined to be immune to EHV-1 infection, if the level of the EHV-1 specific IgG1 is below a respective threshold level, the level of EHV-1 specific IgG4/7 is above a respective threshold level, and the ratio of the level of the EHV-1 specific IgG4/7 versus the level of the EHV-1 specific IgG1 is more than 10. In some embodiments, when the levels of the EHV-1 specific IgG1 and the EHV-1 specific IgG4/7 are below respective threshold levels, three additional markers, namely, interferon α (IFN-α), chemokine (C-C motif) ligand 3 (CCL3) (or chemokine (C-C motif) ligand 2 (CCL2)), and soluble cluster of differentiation 14 (sCD14), are further detected in the sample. In a specific embodiment, the horse is determined to be at an early stage of EHV-1 infection when the level of at least one of IFN-α, CCL3 (or CCL2) and sCD14 is above a respective threshold level. In some embodiments, CCL2 can be substituted for CCL3 with no change in the outcome or interpretation of the assay.

In some embodiments, the horse can be quarantined during an EHV-1 outbreak if the horse is determined to be susceptible to EHV-1 infection or at an early or late stage of EHV-1 infection. In some embodiments, the horse can be quarantined for a longer period if the horse is determined to be susceptible to EHV-1 infection or is determined to be at an early stage infection than if the horse is at a late stage of EHV-1 infection. In some embodiments, the horse is not quarantined if the horse is determined to be immune to EHV-1 infection. In some embodiments, a susceptible horse, or a horse at an early stage of EHV-1 infection, can be quarantined for 15, 20 days (between day 2 and day 21 post infection), or longer, during an EHV-1 outbreak. In some embodiments, the horse at a late stage of EHV-1 infection can be quarantined for 5, 10 or 14 days (between days 8 and 21 post infection) during an EHV-1 outbreak. In a specific embodiment, the horse at a late-stage of EHV-1 infection can be quarantined for not more than 14 days during an EHV-1 outbreak.

In some embodiments, EHV-1 specific IgG1 and the EHV-1 specific IgG4/7 are both directed against a same glycoprotein selected from the group consisting of EHV-1 glycoprotein B (gB), EHV-1 glycoprotein C (gC), and EHV-1 glycoprotein D (gD). In specific embodiments, the glycoprotein is EHV-1 gC; and in some of such specific embodiments, a suitable threshold level for the EHV-1 gC specific IgG1 is 1000 median fluorescent intensities (MFI), and a suitable threshold level for the EHV-1 gC specific IgG4/7 is 1000 MFI.

In some embodiments, the detection of the EHV-1 specific IgG4/7 and the EHV-1 specific IgG1 is achieved by an assay comprising a cytokine/EHV-1 glycoprotein fusion protein. In some embodiments, the cytokine of the fusion protein is selected from the group consisting of IL-2, IL-4, IL-5, IL-6, IL-10, IL-13 and IL-31. In a specific embodiment, the assay detecting the EHV-1 specific IgG4/7 and the EHV-1 specific IgG1 is a multiplex assay.

In some embodiments, the horse has been recently determined to be susceptible to EHV-1 infection or at an early stage of EHV-1 infection. In such embodiments, the levels of IgG1 and IgG4/7, both specific to an EHV-1 glycoprotein, can be detected in an intranasal sample as a follow up in order to determine the current stage of infection or status of immunity. In some embodiments, the initial determination that the horse is susceptible to, or at an early stage of, EHV-1 infection is done by using the biomarkers disclosed herein, after a conventional pathogen test (e.g., a PCR-based method) has determined the causal pathogen as EHV-1.

In some embodiments, an early stage of EHV-1 infection is defined by days between day 2 and day 7 post infection; and the late stage EHV-1 infection is defined by days between day 8 and day 21 post infection.

In some embodiments, a horse susceptible to EHV-1 infection or a horse at an early stage of EHV-1 infection can be quarantined, e.g., for at least 14 days (between day 7 and day 21 post infection); and a horse the late stage of EHV-1 infection can be quarantined, e.g., for at least 1 day and for not more than 14 days.

In another aspect, this disclosure is directed to a method of detecting, in an intranasal sample from a horse, EHV-1 specific IgG1, EHV-1 specific IgG4/7, IFN-α, CCL3 (or CCL2), and sCD14. In some embodiments, the EHV-1 specific IgG1 and the EHV-1 specific IgG4/7 are both directed against a same glycoprotein of EHV-1. In some embodiments, the horse is determined to be susceptible to EHV-1 infection, when levels of the EHV-1 specific IgG1, the EHV-1 specific IgG4/7, IFN-α, CCL3 (or CCL2) and sCD14 are all below respective threshold levels; the horse is determined to be at an early stage of EHV-1 infection, when the level of at least one of IFN-α, CCL3 (or CCL2) and sCD14 is above respective threshold levels and the levels of the EHV-1 specific IgG1 and the EHV-1 specific IgG4/7 are both below respective threshold levels; the horse is determined to be at a late stage of EHV-1 infection, when the levels of the EHV-1 specific IgG1 and the EHV-1 specific IgG4/7 are both above respective threshold levels, and the levels of IFN-α, CCL3 (or CCL2) and sCD14 are all below respective threshold levels; and the horse is determined to be immune to EHV-1 infection, when the level of the EHV-1 specific IgG4/7 is above respective threshold level and the ratio of the level of the EHV-1 specific IgG4/7 versus the level of the EHV-1 specific IgG1 is more than 10, and the levels of EHV-1 specific IgG1, IFN-α, CCL3 (or CCL2) and sCD14 are all below respective threshold levels.

In some embodiments, EHV-1 specific IgG1 and the EHV-1 specific IgG4/7 are both directed against a glycoprotein selected from the group consisting of EHV-1 gB, EHV-1 gC, and EHV-1 gD. In a specific embodiment, the glycoprotein is EHV-1 gC, the threshold level for the EHV-1 specific IgG1 is 1000 MFI, and the threshold level for the EHV-1 specific IgG4/7 is 1000 MFI.

In some embodiments, the early stage of EHV-1 infection is defined as including days between day 2 and day 7 post infection, and the late stage EHV-1 infection is defined as including days between day 8 and day 21 post infection.

In some embodiments, a horse can be quarantined during an EHV-1 outbreak if the horse is susceptible to EHV-1 infection, at an early stage of EHV-1 infection, or at a late stage of EHV-1 infection. In specific embodiments, a horse susceptible to EHV-1 infection and a horse at an early stage of EHV-1 infection can be quarantined for a longer period than a horse at a late stage of EHV-1 infection. In some embodiments, a horse is not quarantined during an EHV-1 outbreak if the horse is immune to EHV-1 infection. In some embodiments, a susceptible horse or a horse at the early stage of EHV-1 infection can be quarantined for at least 15 days; and a horse at a late stage of EHV-1 infection can be quarantined for at least 7 days.

In some embodiments, the detection of the EHV-1 specific IgG4/7 and the EHV-1 specific IgG1 is achieved by an assay comprising a cytokine/EHV-1 glycoprotein fusion protein. In some embodiments, the cytokine of the fusion protein is selected from the group consisting of IL-2, IL-4, IL-5, IL-6, IL-10, IL-13 and IL-31. In a specific embodiment, the assay detecting the EHV-1 specific IgG4/7 and the EHV-1 specific IgG1 is a multiplex assay.

In still another aspect, the disclosure provides a method of detecting, in a blood or serum sample from a horse, EHV-1 specific total immunoglobulin (Ig) and EHV-1 specific IgG4/7. In some embodiments, the EHV-1 specific total Ig and the EHV-1 specific IgG4/7 are both directed against a same glycoprotein of EHV-1. In a specific embodiment, the method further comprises determining whether the horse is susceptible, partially immune or immune to equine herpes virus type 1 (EHV-1) infection. In a specific embodiment, the horse is determined to be susceptible to EHV-1 infection if the levels of the EHV-1 specific total Ig and the EHV-1 specific IgG4/7 are both below respective threshold levels; the horse is determined to be partially immune to EHV-1 infection, when the level of the EHV-1 specific total Ig is below a respective threshold level and the level of the EHV-1 specific IgG4/7 is above a respective threshold level, or when the level of the EHV-1 specific total Ig is above a respective threshold level and the level of the EHV-1 specific IgG4/7 is below a respective threshold level; and the horse is determined to be immune to EHV-1 infection, if the levels of the EHV-1 specific total Ig and the EHV-1 specific IgG4/7 are both above respective threshold levels.

In some embodiments, the glycoprotein is selected from the group consisting of EHV-1 gB, EHV-1 gC, and EHV-1 gD. In specific embodiments, the glycoprotein is EHV-1 gC; and in some of such specific embodiments, a suitable threshold level for the EHV-1 gC specific total Ig is 3000 MFI, and a suitable threshold level for the EHV-1 gC specific IgG4/7 is 400 MFI. In specific embodiments, the glycoprotein is EHV-1 gD; and in some such specific embodiments, a suitable threshold level for the EHV-1 gD specific total Ig is 2000 MFI, and a suitable threshold level for the EHV-1 gD specific IgG4/7 is 200 MFI. In specific embodiments, the glycoprotein is EHV-1 gC; and in some such specific embodiments, a suitable threshold level for the EHV-1 gB specific total Ig is 1400 MFI, and a suitable threshold level for the EHV-1 gB specific IgG4/7 is 100 MFI.

In some embodiments, detection of biomarkers in serum or plasma is used as a basis for a decision to vaccinate a horse against EHV-1. In various embodiments, vaccination is done on a horse which does not show any signs of EHV-1 infection. In some embodiments, a horse is vaccinated against EHV-lif the horse is determined to be susceptible or partially immune to EHV-1 infection, and the horse is not vaccinated if the horse is immune to EHV-1 infection.

In some embodiments, detection of biomarkers in serum or plasma can be used to assist a quarantine decision during an EHV-1 outbreak. In some embodiments, a horse can be quarantined during an EHV-1 outbreak if the horse is determined to be susceptible or partially immune to EHV-1 infection. In some embodiments, the horse susceptible to EHV-1 infection can be quarantined for a longer period than the horse partially immune to EHV-1 infection; and the horse immune to EHV-1 infection is not quarantined during the EHV-1 outbreak. In some embodiments, a horse susceptible to EHV-1 infection can be quarantined for at least 15 days during an EHV-1 outbreak. In some embodiments, a horse susceptible to EHV-1 infection can be quarantined for 15 or 20 days. In some embodiments, a susceptible horse can be quarantined for a longer period of time than the partially-immune horse. In some embodiments, a partially-immune horse can be quarantined for not more than 14 days during an EHV-1 outbreak. In some embodiments, a partially-immune horse can be quarantined for 5, 10 or 14 days. In some embodiments, if a horse is determined to be immune to EHV-1 infection, the horse is not quarantined during an EHV-1 outbreak.

In some embodiments, the detection of the EHV-1 specific IgG4/7 and the EHV-1 specific total Ig in horse serum is achieved by an assay comprising a cytokine/EHV-1 glycoprotein fusion protein. In some embodiments, the cytokine of the fusion protein is selected from the group consisting of IL-2, IL-4, IL-5, IL-6, IL-10, IL-13 and IL-31. In a specific embodiment, the assay detecting the EHV-1 specific IgG4/7 and the EHV-1 specific total Ig is a multiplex assay.

In a further aspect, the disclosure provides a kit comprising a monoclonal anti-IgG1 antibody, a monoclonal anti-IgG4/7 antibody. In some embodiments, the anti-IgG1 antibody and the anti-IgG4/7 antibody are of different species. In some embodiments, the anti-IgG1 antibody is against horse IgG1 and the anti-IgG4/7 antibody is against horse IgG 4/7. In some embodiments, the kit further comprises a monoclonal anti-IFN-α antibody, a monoclonal anti-CCL3 antibody (or a monoclonal anti-CCL2 antibody) and a monoclonal anti-sCD14 antibody.

In some embodiments, the kit further comprises a cytokine/EHV-1 glycoprotein fusion protein. In some embodiments, the glycoprotein of the fusion protein is selected from the group consisting of EHV-1 gB, EHV-1 gC, and EHV-1 gD. In some embodiments, the cytokine of the fusion protein is selected from the group consisting of IL-2, IL-4, IL-5, IL-6, IL-10, IL-13 and IL-31. In some embodiments, the fusion protein is immobilized on a solid support. In a specific embodiment, the solid support is selected from the group consisting of a bead, a microwell plate, and a lateral flow device.

In some embodiments, the kit further comprises labeled detection antibodies against the anti-IgG1 antibody and the anti-IgG4/7 antibody. In some embodiments, the anti-IgG1 antibody comprises CVS45 and the anti-IgG4/7 antibody comprises CVS39. In some embodiments, the monoclonal anti-IFN-α antibody, the monoclonal anti-CCL3 antibody (or a monoclonal anti-CCL2 antibody) and the monoclonal anti-sCD14 antibody are coupled to different color fluorescent beads.

In another aspect, this disclosure is directed to a kit comprising a monoclonal anti-IgG1 antibody, a monoclonal anti-IgG4/7 antibody, a monoclonal anti-IFN-α antibody, a monoclonal anti-CCL3 antibody (or a monoclonal anti-CCL2 antibody), a monoclonal anti-sCD14 antibody, and instructions on how to use the kit.

In yet another aspect, this disclosure is directed to a kit comprising an anti-Ig antibody and a monoclonal anti-IgG4/7 antibody. In some embodiments, the kit further comprises a cytokine/EHV-1 glycoprotein fusion protein. In some embodiments, the glycoprotein of the fusion protein is selected from the group consisting of EHV-1 gB, EHV-1 gC, and EHV-1 gD. In some embodiments, the cytokine of the fusion protein is selected from the group consisting of IL-2, IL-4, IL-5, IL-6, IL-10, IL-13 and IL-31. In some embodiments, the fusion protein is immobilized on a solid support. In a specific embodiment, the solid support is selected from the group consisting of a bead, a microwell plate, and a lateral flow device.

BRIEF DESCRIPTION OF THE DRAWINGS

FIGS. 1A-1K. Biomarkers for EHV-1 infection. (A) IFN-α concentrations in nasal secretions of horses after infection with EHV-1 on day 0 (arrow). The filled circles represent the data from horses infected with the neuropathogenic EHV-1 virus strain Ab4 (n=8). The open white circles represent the data from non-infected control horses (n=8). IFN-α peaks at day 2 post infection and is often detectable on day 3. Significant differences in IFN-α concentrations are marked with a. (B) CCL3 values in nasal secretions of horses after infection with EHV-1 on day 0 (arrow). The filled circles represent the data from horses infected with the neuropathogenic EHV-1 virus strain Ab4 (n=8). The open white circles represent the data from non-infected control horses (n=8). CCL3 peaks at day 3 post infection and is detectable above cut-off values until day 4. In individual horses it is also increased on days 2, 5 or 6 post infection. Significant differences in CCL3 concentrations are marked with a. (C) sCD14 concentrations in nasal secretions of horses after infection with EHV-1 on day 0 (arrow). The filled circles represent the data from horses infected with the neuropathogenic EHV-1 virus strain Ab4 (n=8). The open white circles represent the data from non-infected control horses (n=8). sCD14 peaks at day 3 post infection and is often detectable above cut-off values until day 5. In individual horses it is also increased above cut-off values on day 2. It often stays at low elevated levels until day 10 post infection. Significant differences in sCD14 concentrations are marked with a. (D) Anti-gC IgG1 antibodies in nasal secretion of horses after infection with EHV-1 on day 0 (arrow). The filled circles represent the data from horses infected with the neuropathogenic EHV-1 virus strain Ab4 (n=8). The open white circles represent the data from non-infected control horses (n=8). Significant differences in gC specific IgG1 values are marked with a. (E) Anti-gC IgG4/7 antibodies in nasal secretion of horses after infection with EHV-1 on day 0 (arrow). The filled circles represent the data from horses infected with the neuropathogenic EHV-1 virus strain Ab4 (n=8). The open white circles represent the data from non-infected control horses (n=8). Significant differences in gC specific IgG4/7 values are marked with a. (F) Anti-gC IgG4/7/IgG1 antibody ratios in nasal secretion of horses after infection with EHV-1 on day 0 (arrow). The filled circles represent the data from horses infected with the neuropathogenic EHV-1 virus strain Ab4 (n=8). The open white circles represent the data from non-infected control horses (n=8). Significant differences in gC specific IgG4/7/IgG1 ratios are marked with a. (G) Summary of IFN-α (innermost line), sCD14 (outermost line), and CCL3 (middle line) secretion in the upper respiratory tract of susceptible horses after infection with EHV-1 on day 0 (arrow). Horses (n=8) were infected with the neuropathogenic EHV-1 virus strain Ab4. The lines show mean values of IFN-α, sCD14, and CCL3, respectively. (H) Lack of IFN-α (the line showing IFN-α is completely hidden behind the line showing CCL3), sCD14 (solid black line), and CCL3 (gray line) secretion in the upper respiratory tract of immune/protected horses after infection with EHV-1 on day 0 (arrow). Horses (n=8) were infected with the neuropathogenic EHV-1 virus strain Ab4. The lines show mean values of IFN-α, sCD14, and CCL3, respectively. (I) Anti-EHV-1 gC IgG1 and IgG4/7 in the nasal secretion of susceptible horses after EHV-1 infection (arrow). (J) Anti-EHV-1 gC IgG4/7 in the nasal secretion of immune horses prior to and after EHV-1 infection (arrow). Anti-EHV-1 gC IgG1 antibodies are also shown. (K) CCL2 values in nasal secretions of horses after infection with EHV-1 on day 0 (arrow). The green line represents the horses infected with the neuropathogenic EHV-1 virus strain Ab4 (n=8). The open white circles represent non-infected control horses (n=8). CCL2 peaks at day 3 post infection and is detectable above cut-off values until day 4. Significant differences in CCL3 concentrations are marked with a.

Figures 1A, 1B:
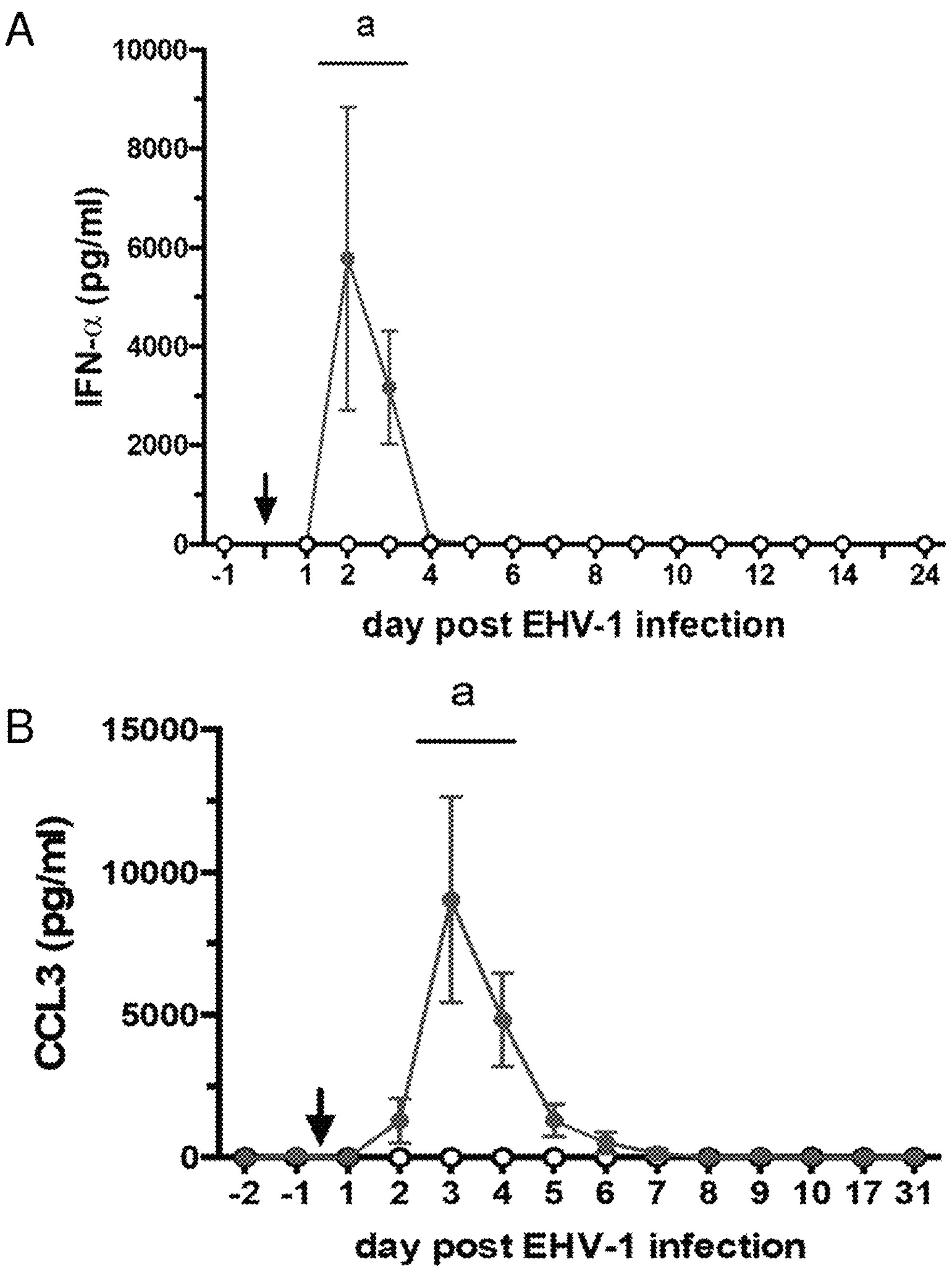

Horses in the Ab4/Ab4 and Ab4ΔORF1/71/Ab4 were infected six months prior to this challenge infection with Ab4 or Ab4ΔORF1/71, respectively. Naïve control horses were not infected previously. Intranasal Ab4 challenge infection with $1\times10^7$ PFU was performed on d0 (arrow). Cytokines were measured in nasal secretion samples using different fluorescent bead-based multiplex assays. Rapid increases in (A) IFN-α, (B) CCL2, and (C) sCD14 were detected in the control/Ab4 group. Significant differences between groups are shown: a=Ab4/Ab4 and control/Ab4; b=Ab4ΔORF1/71/Ab4 and control/Ab4.

FIGS. 6A-6D. Total Ig and IgG isotypes were measured by EHV-1 multiplex assays in nasal secretion samples. Preexisting nasal anti-gC antibodies were measured in all 15 horses prior to Ab4 challenge on d-2 (2 days before Ab4 challenge) by experimental group. (A) Total Ig; (B) IgG1; (C) IgG4/7; (D) IgG 3/5.

DETAILED DESCRIPTION

As used herein, the term "about" refers to an approximately ±10% variation from a given value.

The term "animal" includes mammals, for example, human, horse, camel, dog, pig, cow, and sheep. In some embodiments, the animal is an animal suspected to have contracted a disease (e.g., an infection with a pathogen).

The term "antibody" is used in the broadest sense and includes monoclonal antibodies (including agonist, antagonist, and neutralizing antibodies), polyclonal antibodies, multivalent antibodies, multispecific antibodies, and antibody fragments so long as they exhibit the desired binding specificity.

The term "biological sample" includes body samples from an animal, including biological fluids such as serum, plasma, intranasal fluids, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts. In some embodiments, the biological sample is a blood, serum, plasma or intranasal sample.

The term "early stage of EHV-1 infection" refers to days between day 2 and day 7 post EHV-1 infection and the term "late stage EHV-1 infection" refers to days between day 8 and day 21 post EHV-1 infection. A horse in a late stage of infection is immune to further EHV-1 infection, i.e., it cannot be re-infected with the EHV-1 virus again.

The term "EHV-1 specific IgG1" refers to an immunoglobulin G (IgG) 1 type antibody specific to an epitope of EHV-1. The term "EHV-1 specific IgG4/7" refers to an immunoglobulin G (IgG) 4/7 type antibody specific to an epitope of EHV-1. The term "EHV-1 specific total Ig" refers to immunoglobulin molecules of all types combined that are specific to an epitope of EHV-1. In some embodiments where an intranasal sample is used for detection, the EHV-1 specific IgG1 and the EHV-1 specific IgG4/7 are both against one same EHV-1 glycoprotein selected from the group consisting of EHV-1 glycoprotein B (gB), EHV-1 glycoprotein C (gC), and EHV-1 glycoprotein D (gD). In some embodiments where a blood or serum sample is used for detection, the EHV-1 specific total Ig and the EHV-1 specific IgG4/7 are both against one same EHV-1 glycoprotein selected from the group consisting of EHV-1 glycoprotein B (gB), EHV-1 glycoprotein C (gC), and EHV-1 glycoprotein D (gD).

The term "fusion protein" or "fusion polypeptide" refers to a protein having at least two heterologous polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides.

The term "immune to EHV-1 infection" or "fully protected from EHV-1 infection" refers to an animal which is not undergoing an EHV-1 infection at the present and is protected from future infections with the EHV-1 virus. The term "susceptible to EHV-1 infection" refers to an animal which is not protected from an EHV-1 infection. As used herein, animals that are undergoing an infection, either at an early stage or a late stage, are not considered to fall within either the "susceptible to EHV-1 infection" category or the "immune to EHV-1 infection" category. The term "partially immune" refers to an animal which is partially protected or partially immune from future EHV-1 infections.

Biomarkers Useful for Monitoring EHV-1 Infections and Immunity to EHV-1

The present disclosure describes biomarkers useful for detecting and staging EHV-1 infections as well as determining the immunity status of horses towards EHV-1 infection. The biomarkers of the present disclosure can be detected from various biological samples including nasal secretion (intranasal sample) and serum or blood. Specifically, one can identify and distinguish (i) susceptible horses (will develop disease during an outbreak) from those that are in (ii) the early infection stage (high shedders of virulent pathogen), (iii) the later infection stage (developing immunity, low or no shedding), and (iv) immune horses that will not develop disease or shed virus with the use of the disclosed biomarkers.

The use of these biomarkers in the identification of horses in the different infection stages supports the better characterization of these groups in an outbreak situation, helps improve management of these groups including treatment of horses during the early and late infection stage, allows to release immune horses earlier from quarantine, and gives veterinarians and horse owners a better tool to evaluate risk and prognosis for each individual horse. Importantly, the methods of the present disclosure can significantly decrease the costs and efforts needed during EHV-1 outbreaks.

In some embodiments, the biomarkers of the disclosure comprise one or more of equine herpes virus type 1 (EHV-1) specific immunoglobulin G1 (IgG1), EHV-1 specific immunoglobulin G4/7 (IgG4/7), interferon α (IFN-α), chemokine (C-C motif) ligand 3 (CCL3), chemokine (C-C motif) ligand 2 (CCL2), soluble cluster of differentiation 14 (sCD14), and EHV-1 specific total Ig.

Methods of Monitoring an EHV-1 Infection from an Intranasal Sample Using Biomarkers In one aspect, this disclosure is directed to methods of determining whether a horse is susceptible or immune to an EHV-1 infection, or is undergoing an EHV-1 infection, by detecting biomarkers in an intranasal sample of the horse. In specific embodiments, the biomarkers being detected are IgG1 and IgG4/7, both specific to an EHV-1 glycoprotein. The levels of these two biomarkers, when compared to respective threshold levels, together with the ratio of the two biomarkers in some instances, permit a determination as to whether a horse is within the susceptible category or early infection category, within the late-stage infection category, or within the immune category. In order to further distinguish between the susceptible category and the early infection category, additional biomarkers that can be assessed include one or more of IFN-α, CCL3 (or CCL2) and sCD14.

To illustrate, exemplary suitable threshold levels for gC based assays are summarized in Table 1.

TABLE 1

The biomarkers IFN-α, sCD14, CCL2 or CCL3, and EHV-1 gC specific IgG1 and IgG4/7 distinguish between the four stages of EHV-1 infection in nasal secretion. The unit for the threshold levels for IgG1 and IgG4/7 is median fluorescent intensities (MFI), and the unit for the threshold levels for IFN-α, sCD14, CCL2 and CCL3 is pg/ml.

| EHV-1 infection stage | (i) susceptible | (ii) early infection d2–7 pi | (iii) late infection (a) d8–13 pi | (iii) late infection (b)d14–20 pi | (iv) immune >d21 pi |
|---|---|---|---|---|---|
| Detectable biomarker | | IFN-α and/or CCL2 and/or CCL3 and/or sCD14 | IgG1 IgG4/7 | IgG1 IgG4/7 IgG4/7/ IgG1 Ratio (>2) | IgG4/7 IgG4/7/ IgG1 ratio (>10) |
| Non-detectable or low (with cut-off values) | IFN-α (<100) CCL2 (<100) CCL3 (<100) IgG1 (<1000) IgG4/7 (<1000) sCD14 (<2000) | IgG1 IgG4/7 | IFN-α CCL2 CCL3 sCD14 | | IFN-α CCL2 CCL3 sCD14 IgG1 |
| Interpretation biomarker analysis | Will develop disease if infected | high shedders of virulent pathogen | developing immunity, low or no shedding (PCR positive or negative) | | no disease or viral shedding |
| EHV-1 PCR result | PCR negative | PCR positive (virus shedding) | PCR positive (residual DNA) or negative | | PCR negative |
| PCR interpretation | Not shedding EHV-1 | a horse with positive PCR result is always handled as a potentially shedder of virulent pathogen | | | |
| PCR limitations | no information on immune status and/or susceptibility | | | | |

Methods of Determining EHV-1 Immunity Status from Serum or Plasma Analysis

In another aspect, this disclosure is directed to methods of determining whether a horse is susceptible, partially immune, or immune to an EHV-1 infection by detecting biomarkers in the horse's serum. In specific embodiments, the biomarkers being detected are total Ig and IgG4/7, both specific to an EHV-1 glycoprotein. In some embodiments, the disclosed methods are performed on horses which do not show any signs of EHV-1 infection.

To illustrate, exemplary suitable threshold levels for gC, gD and gB based assays are summarized in Tables 2 and 3.

TABLE 2

Quantitative EHV-1 serum biomarker to identify susceptible and protected horses and recommended EHV vaccination. The disclosed thresholds are based on anti-gC antibodies.

| Interpretation | Anti-gC total Ig | Anti-gC IgG4/7 | EHV vaccination |
|---|---|---|---|
| EHV-1 susceptible | <3000 MFI | <400 MFI | Vaccination needed to increase anti-gC total Ig and IgG4/7 |
| EHV-1 protected | ≥3000 MFI | ≥400 MFI | Not needed, recheck in 3-9 months depending on values |
| Partially protected | <3000 MFI & ≥400 MFI or ≥3000 MFI & <400 MFI | | Vaccination recommended within the next 2 months |

TABLE 3

Quantitative EHV-1 serum biomarker to identify susceptible and protected horses. The disclosed thresholds are based on anti-gD and anti-gB antibodies.

| | Anti-gD total Ig | Anti-gD IgG4/7 | Anti-gB total Ig | Anti-gB IgG4/7 |
|---|---|---|---|---|
| EHV-1 susceptible | <2000 MFI | <200 MFI | <1400 MFI | <100 MFI |
| EHV-1 protected | ≥2000 MFI | ≥200 MFI | ≥1400 MFI | ≥100 MFI |
| Partially protected | <2000 MFI & ≥200 MFI or ≥2000 MFI & <200 MFI | | <1400 MFI & ≥100 MFI or ≥1400 MFI & <100 MFI | |

Multiplex Assays and Cytokine Fusion Proteins

In some embodiments, the methods disclosed herein utilize multiplex assays. In some embodiments, the multiplex assays comprise fusion proteins. In some embodiments, the fusion proteins are cytokine fusion proteins. Reagents for multiplex assays, including protocols and reagents are described in U.S. Pub. No.: US 2017/0067896, Wagner et al. (*Vet Immunol Immunopathol.* 2011 Dec. 15; 144(3-4):374-81) and Wagner B and Freer H. (*Vet. Immunol. Immunopathol.,* 2009, 127: 242-248), which are all incorporated by reference.

In some embodiments, the assay to detect the EHV-1 specific IgG1 (or EHV-1 specific total Ig) and the EHV-1 specific IgG4/7 is a multiplex assay. In some embodiments, the EHV-1 specific IgG1 (or EHV-1 specific total Ig) and the EHV-1 specific IgG4/7 are detected using an assay comprising a cytokine/EHV-1 glycoprotein fusion protein. In some embodiments, the EHV-1 glycoprotein of the fusion protein is selected from the group consisting of EHV-1 glycoprotein B (gB), EHV-1 glycoprotein C (gC), and EHV-1 glycoprotein D (gD). In a specific embodiment, the glycoprotein is EHV-1 gC. In some embodiments, the cytokine of the fusion protein is selected from the group consisting of IL-2, IL-4, IL-5, IL-6, IL-10, IL-13 and IL-31. In a specific embodiment, the cytokine is IL-4. In some embodiments, the cytokine is not coupled to a cytokine.

In some embodiments, the assay to detect the EHV-1 specific IgG1 (or EHV-1 specific total Ig) and the EHV-1 specific IgG4/7 is enzyme-linked immunosorbent assay (ELISA).

In some embodiments, the assay to detect the EHV-1 specific IgG1 (or EHV-1 specific total Ig) and the EHV-1 specific IgG4/7 is a lateral flow assay.

Methods for Determining Efficacy of an EHV-1 Vaccine

In some embodiments, the methods and kits of the present disclosure can be used to determine the efficacy of an EHV-1 vaccine in an animal in inducing immunity against an EHV-1 infection. An effective EHV-1 vaccine induces immunity against an EHV-1 infection. In some embodiments, the vaccine-induced EHV-1 immunity lasts for at least 6 months. In some embodiments, the vaccine-induced EHV-1 immunity lasts for 6 months, 7 months, 8 months, 9 months, 10 months, 11 months, 12 months, 15 months, 2 years, 3 years or the lifetime of the animal (i.e., until the animal dies).

In some embodiments, the vaccine efficacy is determined from an intranasal sample. In some embodiments, the vaccine efficacy is determined from a blood sample. In some embodiments, the vaccine efficacy is determined from a serum or plasma sample.

In some embodiments, the vaccine efficacy is determined at least 3 days after vaccination. In some embodiments, the vaccine efficacy is determined 3 days after, 4 days after, 5 days after, 6 days after, 7 days after, 8 days after, 9 days after, 10 days after, 11 days after, 12 days after, 13 days after, 14 days after, or 21 days after vaccination. In some embodiments, the vaccine efficacy is determined over a time course. In some embodiments, the time course comprises days between 3 days after vaccination and 21 days after vaccination. In some embodiments, samples for determining vaccine efficacy are collected daily, every other day, every three days, or once a week.

In some embodiments, vaccine efficacy is tested over an extended period of time to determine whether and when a new vaccination is necessary. In some embodiments, a new EHV-1 vaccination is administered to the animal if the animal is found to be susceptible to EHV-1 infection. In some embodiments, vaccine efficacy is tested every month, every other month, every three months, every six months or every year.

In one aspect, this disclosure provides a method comprising detecting, in an intranasal sample from a horse, equine herpes virus type 1 (EHV-1) specific immunoglobulin G1 (IgG1) and EHV-1 specific immunoglobulin G4/7 (IgG4/7) in order to test efficacy of a vaccine. In some embodiments, the EHV-1 specific IgG1 and the EHV-1 specific IgG4/7 are both directed against a same glycoprotein of EHV-1. In some embodiments, the method further comprises determining whether the horse is susceptible or immune to EHV-1 infection after an EHV-vaccination. In a specific embodiment, a horse is determined to be susceptible to EHV-1 infection (i.e., that the EHV-1 vaccine has failed to immunize the animal against an EHV-1 infection) if the levels of the EHV-1 specific IgG1 and the EHV-1 specific IgG4/7 are both below respective threshold levels; and the horse is determined to be immune to EHV-1 infection (i.e., that the EHV-1 vaccine has successfully immunized the animal against an EHV-1 infection), if the level of the EHV-1 specific IgG1 is below a respective threshold level, the level of EHV-1 specific IgG4/7 is above a respective threshold level, and the ratio of the level of the EHV-1 specific IgG4/7 versus the level of the EHV-1 specific IgG1 is more than 10.

In still another aspect, the disclosure provides a method of determining the efficacy of an EHV-1 vaccine comprising detecting, in a blood or serum sample from a horse, EHV-1 specific total immunoglobulin (Ig) and EHV-1 specific IgG4/7. In some embodiments, the EHV-1 specific total Ig and the EHV-1 specific IgG4/7 are both directed against a same glycoprotein of EHV-1. In a specific embodiment, the method further comprises determining whether the horse is susceptible (i.e., the EHV-1 vaccine has failed to immunize the animal against an EHV-1 infection), or immune to equine herpes virus type 1 (EHV-1) infection. In a specific embodiment, the horse is determined to be susceptible to EHV-1 infection if the levels of the EHV-1 specific total Ig and the EHV-1 specific IgG4/7 are both below respective threshold levels; the horse is determined to be partially immune to EHV-1 infection, when the level of the EHV-1 specific total Ig is below a respective threshold level and the level of the EHV-1 specific IgG4/7 is above a respective threshold level, or when the level of the EHV-1 specific total Ig is above a respective threshold level and the level of the EHV-1 specific IgG4/7 is below a respective threshold level; and the horse is determined to be immune to EHV-1 infection, if the levels of the EHV-1 specific total Ig and the EHV-1 specific IgG4/7 are both above respective threshold levels. In some embodiments, the threshold levels are selected from values recited in Table 2 or Table 3.

Kits

In a further aspect, the disclosure provides a kit for performing the methods of the disclosure, comprising a monoclonal anti-IgG1 antibody, a monoclonal anti-IgG4/7 antibody. In some embodiments, the anti-IgG1 antibody and the anti-IgG4/7 antibody are of different species. For instance, the anti-IgG1 antibody or the anti-IgG4/7 antibody may be mouse, rabbit, dog, donkey, goat, pig or chicken antibodies. In some embodiments, the anti-IgG1 antibody is against horse IgG1 and the anti-IgG4/7 antibody is against horse IgG 4/7. In some embodiments, the kit further comprises a monoclonal anti-IFN-α antibody, a monoclonal anti-CCL3 antibody (or a monoclonal anti-CCL2 antibody) and a monoclonal anti-sCD14 antibody.

In some embodiments, the kit further comprises a cytokine/EHV-1 glycoprotein fusion protein. In some embodiments, the glycoprotein of the fusion protein is selected from the group consisting of EHV-1 gB, EHV-1 gC, and EHV-1 gD. In some embodiments, the cytokine of the fusion protein is selected from the group consisting of IL-2, IL-4, IL-5, IL-6, IL-10, IL-13 and IL-31. In some embodiments, the fusion protein is immobilized on a solid support. In a specific embodiment, the solid support is selected from the group consisting of a bead, a microwell plate, and a lateral flow device.

In some embodiments, the kit further comprises labeled detection antibodies against the anti-IgG1 antibody and the anti-IgG4/7 antibody. In some embodiments, the anti-IgG1 antibody comprises CVS45 and the anti-IgG4/7 antibody comprises CVS39. In some embodiments, the monoclonal anti-IFN-α antibody, the monoclonal anti-CCL3 antibody (or the monoclonal anti-CCL2 antibody) and the monoclonal anti-sCD14 antibody are coupled to different color fluorescent beads.

In another aspect, this disclosure is directed to a kit comprising a monoclonal anti-IgG1 antibody, a monoclonal anti-IgG4/7 antibody, a monoclonal anti-IFN-α antibody, a monoclonal anti-CCL3 antibody (or a monoclonal anti-CCL2 antibody), a monoclonal anti-sCD14 antibody, and instructions on how to use the kit.

In yet another aspect, this disclosure is directed to a kit comprising an anti-Ig antibody and a monoclonal anti-IgG4/7 antibody. In some embodiments, the kit further comprises a cytokine/EHV-1 glycoprotein fusion protein. In some embodiments, the glycoprotein of the fusion protein is selected from the group consisting of EHV-1 gB, EHV-1 gC, and EHV-1 gD. In some embodiments, the cytokine of the fusion protein is selected from the group consisting of IL-2, IL-4, IL-5, IL-6, IL-10, IL-13 and IL-31. In some embodiments, the fusion protein is immobilized on a solid support. In a specific embodiment, the solid support is selected from the group consisting of a bead, a microwell plate, and a lateral flow device.

Unless defined otherwise, all technical and scientific terms used herein have the same meaning as commonly understood by one skilled in the art to which this disclosure belongs. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Fluorescent Bead-Based Multiplex Assay

IFN-α, CCL3 (or CCL2) and sCD14 in nasal secretions were quantified with a fluorescent bead-based multiplex assay.

EHV-1 specific antibodies in serum or nasal secretion samples were determined using a fluorescent bead-based EHV-1 multiplex assay.

Cloning and Expression of EHV-1 gC

RNA was purified from equine peripheral blood mononuclear cells infected with EHV-1 strain Ab4 (NCBI accession AY665713) and reverse transcribed using SuperScript III (Invitrogen, Waltham, MA). The extracellular regions of gC (corresponding to amino acid (aa) residues 30-431) was cloned into a mammalian pcDNA3.1-based vector (Invitrogen, Carlsbad, CA) containing the equine IL-4 gene as a tag for detection and purification as previously described (Wagner, B., et al., *Vaccine,* 33.42 (2015): 5588-5597.). Chinese hamster ovary (CHO) cells are transfected with purified linear DNA from each construct using the Geneporter II transfection reagent (Gene Therapy Systems, San Diego, CA, USA). Transfected CHO cells are subsequently plated into 96-well plates for neomycin selection of stable clones. Expression of the fusion protein is monitored by intracellular anti-IL-4 staining of cells by flow cytometry and by IL-4 multiplex analysis of supernatants (Wagner B. et al., *Vet. Immunol. Immunopathol.,* 146: 125-134). Clones with the highest secretion of the fusion protein are further purified by 2-3 rounds of limiting dilution. A stable transfectant expressing EHV-1 gC/IL-4 fusion protein is grown until 60-70% confluent in MEM medium containing 5% fetal calf serum. Then, cell culture supernatants containing the secreted gC/IL-4 are harvested until cells are 100% confluent and of good viability.

The invention can also be performed or expanded to other glycoproteins of EHV-1, e.g. gD and/or gB. gD and gB were cloned and expressed as described above.

Bead Coupling

The different coupling antibodies (Table 4) were coupled to individual fluorescent color-coded beads (e.g. Luminex Corp., Austin, TX, USA). For example: IFN-α mAb 240-2 was coupled to bead 33, CCL3 mAb 77 was coupled to bead 42, CD14 mAb 105 was coupled to bead 38, IL-4 mAb 25 was coupled to bead 34 or 35.

The entire bead coupling procedure was performed at room temperature. All centrifugations were performed at 14,000×g for 4 minutes. After centrifugation, the beads were resupended by vortexing and sonication for 20 seconds. For activation, $5\times10^6$ beads were washed once in H2O. Beads were resuspended in 80 μl of 100 mM sodium phosphate buffer, pH 6.2. Then, 10 μl Sulfo-NHS (50 mg/ml,) and 10 μl 1-ethyl-3-[3-dimethylaminopropyl]carbodiimide hydrochloride (EDC, 50 mg/ml, e.g. both from Pierce Biotechnology Inc., Rockford, IL) were added and incubated for 20 min. The beads were washed twice with 50 mM 2-[N-morpholino]ethanesulfonic acid pH 5.0 (MES) and are resuspended in MES solution. These activated beads were used for antibody coupling of 50 g mAb. The coupling of the mAbs was performed for three hours with rotation. After coupling, the beads were resuspended in blocking buffer (PBS with 1% (w/v) BSA and 0.05% (w/v) sodium azide) and incubated for 30 min. The beads were washed three time in PBS with 0.1% (w/v) BSA, 0.02% (v/v) Tween 20 and 0.05% (w/v) sodium azide (PBS-T), counted and stored in the dark at 2-8° C. The bead coupling protocol can be scaled up by using any multiples of the bead numbers, buffer volumes and mAb amounts stated above.

TABLE 4

EHV-1 Biomarker reagents and test kit. mAb = monoclonal antibody

| Biomarker | IFN-α | CCL3 | sCD14 | Anti-gC IgGL1 | Anti-gC IgG4/7 |
|---|---|---|---|---|---|
| Bead | 33 | 42 | 38 | 34 | 3 |
| Coupling reagent | IFN-α mAb 240-2 | CCL3 mAb 77 | CD14 mAb 105 | IL-4 mAb 25 EHV-1 gC/IL-4 | IL-4 mAb 25 EHV-1 gC/IL-44 |
| Samples | Nasal secretion | | | Nasal secretion or serum | |
| Detection reagent | IFN-α mAb 150 | CCL3 mAb 289-2 | CD14 mAb 59 | Anti-IgG1 mAb | Anti-IgG4/7 mAb |

A special second step was then performed for IL-4 beads, only. IL-4 beads were next incubated with an IL-4 fusion protein of EHV-1 gC (IL-4/gC). This was performed by vortexing and sonicating the IL-4 beads and transferring them into sterile round-bottom plastic tubes. Supernatants containing recombinant IL-4/EHV-1 gC were then added to the IL-4 beads in a ratio of 10:1 and the mixture is incubated on a platform rocker shaker at room temperature for 30 minutes without light exposure. Then, the beads were spun down, the supernatant is removed and the beads were washed three times with blocking buffer. Beads were resuspended in blocking buffer, counted and stored in the dark at 2-8° C.

In some embodiments, the assay can be performed multiplexing gC with gD and/or gB. In some embodiments, bead 36 is coupled with IL-4/gD and bead 33 with IL-4/gB. The remaining procedure of bead coupling is the same as above for gD and gB.

Standards for Biomarker Quantification

Supernatants of recombinant equine IFN-α, CCL3 (or CCL2) and sCD14 are used as standards in the multiplex assay in concentration range from 100 ng/ml to 0.25 pg/ml. This is achieved by eight 1:5 dilution steps. Sample concentrations are expressed in pg/ml.

Serum samples with known content (low, medium, and high EHV-1 IgG1 and IgG4/7) are used as standards for quantification. These are added as assay controls with a specific EHV-1 IgG1 and IgG4/7 content for each of the standards expressed as median fluorescent intensities (MFI). The known MFI values for each standard serum result from multiple standard runs (>10) which are used to create a mean MFI for each standard serum. Standard values within the 80% confidence interval of the mean value are accepted for sample quantification on the respective assay. Sample values are expressed as MFI. Alternatively, the IgG1 and IgG4/7 standards can be used for relative quantification of the IgG1 and IgG4/7 antibodies in the samples.

In some embodiments, the standard sera also serve as standards for the gD and gB assays.

Multiplex Assay (IFN-α, CCL3 (or CCL2), sCD14, gC IgG1 & IgG4/7)

The IFN-α, CCL3 (or CCL2), sCD14 and IL-4/gC beads can be multiplexed for nasal secretion samples. Nasal secretion samples are run undiluted. For serum samples, the IL-4/gC beads are used. Serum is diluted at 1:400. Biotinylated detection mAbs are outlined in Table 4.

In more detail, the coupled beads were sonicated, mixed and diluted in blocking buffer to a final concentration of $1\times10^5$ beads/ml each. For the assay, $5\times10^3$ beads/each were used per microtiter well. The recombinant standard proteins and standard sera were prepared in blocking buffer using three-fold dilutions of the proteins. Assay plates, e.g. Millipore Multiscreen HTS plates (Millipore, Danvers, MA), were soaked with PBS-T using a plate washer, e.g. EL×50 plate washer (Biotek Instruments Inc., Winooski, VT), for 2 minutes. The solution was aspirated from the plates and 50 μl of each diluted standard concentration or 50 μl sample were applied to the plates. Then, 50 μl of mixed bead solution was added to each well and incubated for 30 minutes on a shaker at room temperature. Then, the plates were washed 3-5 times with PBS-T. Afterwards, 50 μl of the detection antibody mixture (Table 4) diluted in blocking buffer was added to each well and incubated for 30 minutes as above. All detection mAbs were biotinylated. After washing, 50 ml streptavidin-phycoerythrin (e.g. Invitrogen, Carlsbad, CA) were added to the plates. Plates were incubated for 30 minutes as above and washed again. Finally, the beads were resuspended in 100 ml blocking buffer and the plates were placed on the shaker for 15 minutes. The assay was analyzed in a multiplex analyzer, e.g. Luminex 200 instrument (Luminex Corp.). The data were reported as median fluorescent intensities (MFI). For standard curve fitting and subsequent calculation of the cytokine concentrations in samples the logistic 5p formula ($y=a+b/(1+(x/c)^d)^f$) was used (e.g. Luminex 100 Integrated System 2.3).

Quantification of EHV-1 gC-Specific Total Ig and IgG4/7 in the Bead-Based Assay

For antibody detection in the EHV-1 gC assay, all serum samples and the three standard sera were diluted 1:400 in PBN blocking buffer (PBS with 1% (w/v) BSA and 0.05% (w/v) sodium azide). A PBN buffer control is also included in the assay run. Millipore Multiscreen HTS plates (Millipore, Danvers, MA) were soaked with PBST (PBS with 0.02% (v/v) Tween 20 for at least 2 minutes. After aspirating the PBST, 50 μl of the diluted serum samples, standard sera, or PBN buffer control were added. The EHV-1 gC beads are vortexed and sonicated for 20 seconds, and 50 μl bead solution containing $5\times10^3$ of EHV-1 gC beads were added per assay well. The plate was covered to protect it from light and was incubated at room temperature with shaking for 30 min. Plates were washed using the Biotek EL×50 plate washer (Biotek Instruments Inc., Winooski, VT). For total Ig detection, 50 μl of a biotinylated goat anti-horse IgG(H+L) antibody (Jackson Immunoresearch Laboratories, West Grove, PA) was added to the plate at 1:10,000 dilution in PBN. For IgG4/7 isotype detection, the plate was incubated with a biotinylated monoclonal antibody against equine IgG4/7 (e.g. CVS39) during this step. The plate was incubated with the respective detection antibody as described above and washed afterwards. Another 50 μl of streptavidin-phycoerythrin (PE) (Invitrogen, Carlsbad, CA) was finally added to each well at a dilution of 1:100 in PBN. The plate was incubated as above and washed afterwards. Then, 100 μl of PBN are added to each well, the plate was covered and placed on a shaker for 15 minutes to re-suspend the beads. The assay was analyzed in a Luminex 200 instrument (Luminex Corp.) using BioPlex Manager 6.1 software (Bio-Rad, Hercules, CA). Results were reported as MFI. Data were reported as median fluorescent intensities (MFI).

In some embodiments, gC beads were multiplexed with gD and/or gB beads. For multiplexing with gD and/or gB, the respective beads were mixed with the gC beads before the beads were added to the plate wells and the bead mixture is added. Serum antibodies to all glycoproteins were then measured in the serum samples simultaneously. The remaining procedure was the same as above.

Horses, Groups and Initial EHV-1 Infection

Fifteen horses from the EHV-1-controlled herd of Icelandic horses at Cornell University (Wagner et al. 2015, Wagner et al. 2017) were enrolled in this study. Six months prior to the EHV-1 challenge infection described here, all 15 horses were EHV-1 naïve, randomly assigned to three groups (n=5), and participated in an initial experimental EHV-1 infection previously described by Wimer et al. (Wimer et al., *PlosOne,* 13(11):e0206679, 2018). Briefly, one group of horses was not infected with EHV-1 (control). A second group was infected with the neurogenic EHV-1 strain Ab4 (Nugent et al. 2006). The third group was infected with Ab4ΔORF1/71 (Table 5).

TABLE 5

Three groups of EHV-1 naïve horses were infected with different EHV-1 viruses (1 × $10^7$ PFU) and then challenged with the neuropathogenic EHV-1 strain Ab4 six months later.

| Group | n | Age (yrs)[a] | Gender[b] | Initial infection | Challenge 6-months pii[c] |
|---|---|---|---|---|---|
| Non-inf. Ctrl/Ab4 | 5 | 2.5 | 2 m, 3 g | saline | Ab4 |
| Ab4ΔORF1/71/Ab4 | 5 | 2.5 | 1 m; 4 g | Ab4ΔORF1/71 | Ab4 |
| Ah4/Ab4 | 5 | 2.5 | 2 m; 3 g | Ab4 | Ab4 |

[a]age in years at initial infection, [b]m = mare; g = gelding, [c]pii = post initial infection Overall, Ab4ΔORF1/71 was less virulent than the parent Ab4 virus. However, immune induction was markedly similar between the Ab4ΔORF1/71 and Ab4 infected groups. After release from initial EHV-1 infection and prior to the EHV-1 challenge infection described here, the horses were kept on pasture separated by group at an isolated facility at Cornell University without contact to other horses in the US prior to and for the duration of this study. The facility had restricted access for people to avoid infection with common US pathogens and to maintain the EHV-1-controlled status of the Icelandic herd. Grass hay was fed ad libitum. Horses were vaccinated against rabies, West Nile virus, Eastern and Western Encephalitis virus, and tetanus. They were dewormed on a regular basis but were not vaccinated or treated otherwise.

Samples

160 Blood and nasal secretion (swab) samples were obtained and processed as previously described (Wimer et al., *PlosOne,* 13(11):e0206679, 2018). Blood samples included sodium heparinized samples for PBMC isolation and those without anti-coagulant for serum collection. Baseline blood and nasal secretion samples were taken two days before EHV-1 challenge infection (d-2). Serum samples were also taken on the day of challenge (d0) prior to infection. Afterwards, blood and nasal secretion samples were taken daily (d1-d10pi), and on d15 and d22pi (pi=post-infection). Additional blood samples were taken on d57 and d92pi. Horses were released from the isolation barn on d10pi after sampling and kept in their experimental groups on separate pastures without contact between the different groups.

Clinical Evaluation

170 Baseline physical examination measurements were taken on d-1, immediately before EHV-1 infection (d0), and in the mornings of d1-10pi. Body temperatures were taken in the morning and evening until d7pi and then once daily in the mornings before samples were obtained. Clinical scoring, including gait evaluation for ataxia, was done as previously described (Wimer et al., *PlosOne,* 2018, 13(11): e0206679) according to the system described by Furr and coworkers (Furr and Reed, *Neurologic Examination. In: Equine Neurology,* 2008, pp. 65-76). The clinicians taking samples and performing the scoring were not aware of the group assignments of the horses during the prior initial EHV-1 infection (Table 5). A fever was defined as a rectal temperature of >38.5° C.

Example 2: Nasal Biomarkers During EHV-1 Infection in Horses

Figures 1C, 1D:
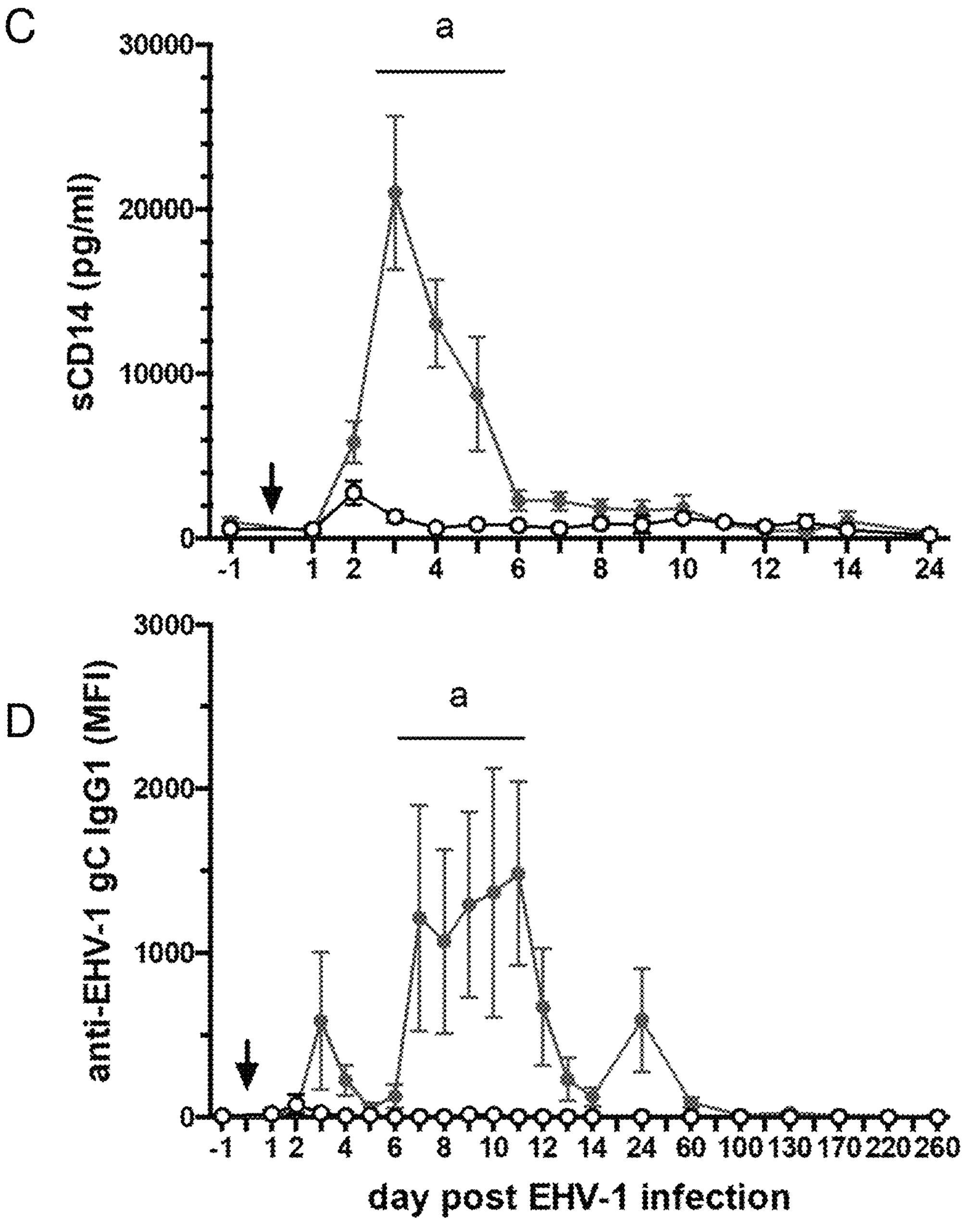
Figures 1E, 1F:
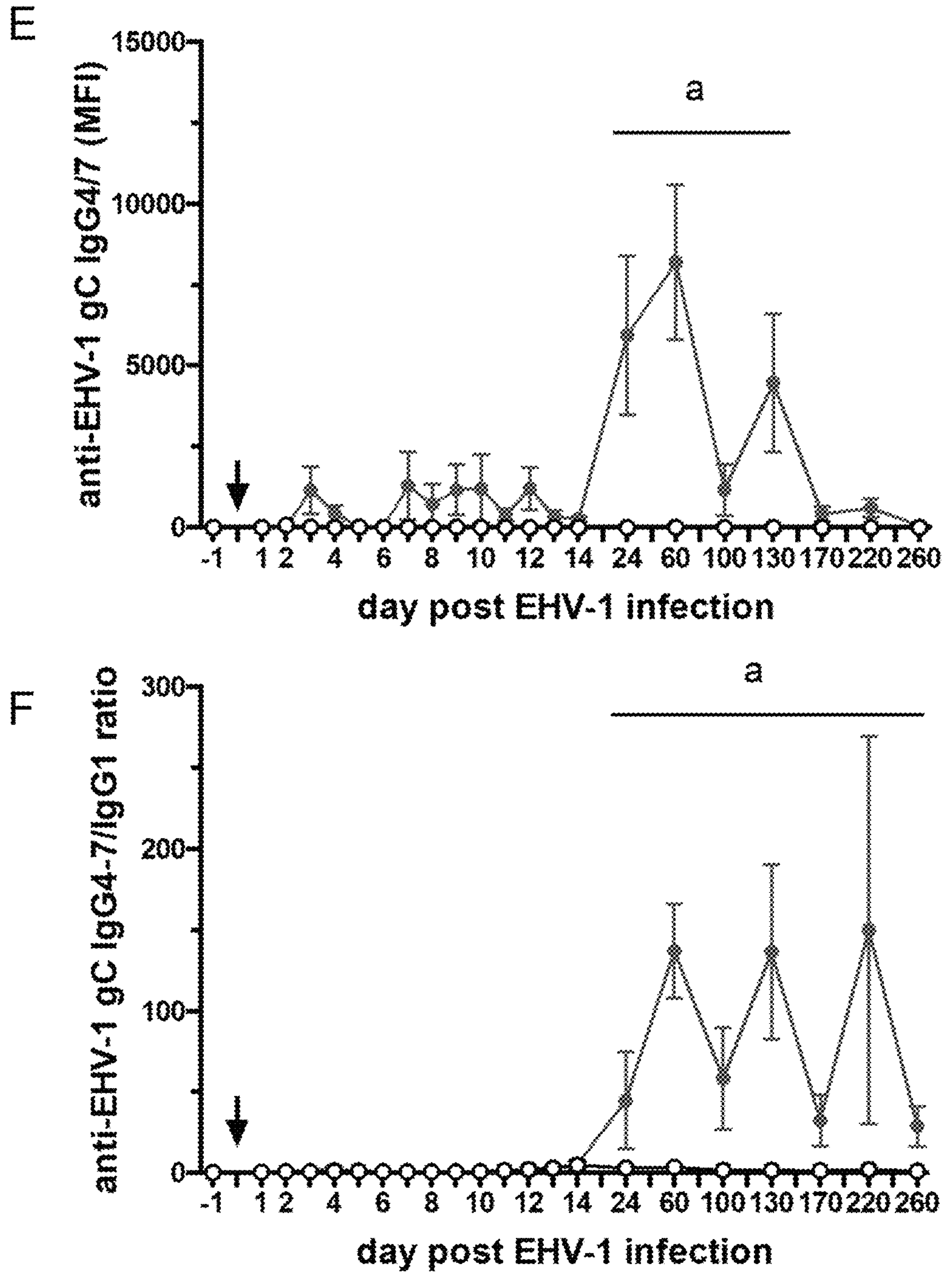

The inventors identified that the concentrations of several biomarkers changed in nasal secretions and serum of EHV-1 infected horses, depending on the stage of the infection. For instance, it was discovered that the concentrations of IFN-α (FIG. 1A), CCL3 (FIG. 1B), sCD14 (FIG. 1C), and EHV-1 gC specific IgG1 (FIG. 1D) and IgG4/7 (FIG. 1D) peaked at different times during the course of an EHV-1 infection. In contrast, none of these biomarkers were detectable in naïve horses (horses that were never infected with EHV-1), whereas in the early infection period IFN-α and/or CCL3 and/or sCD14 were detectable.

Figures 1G, 1H:
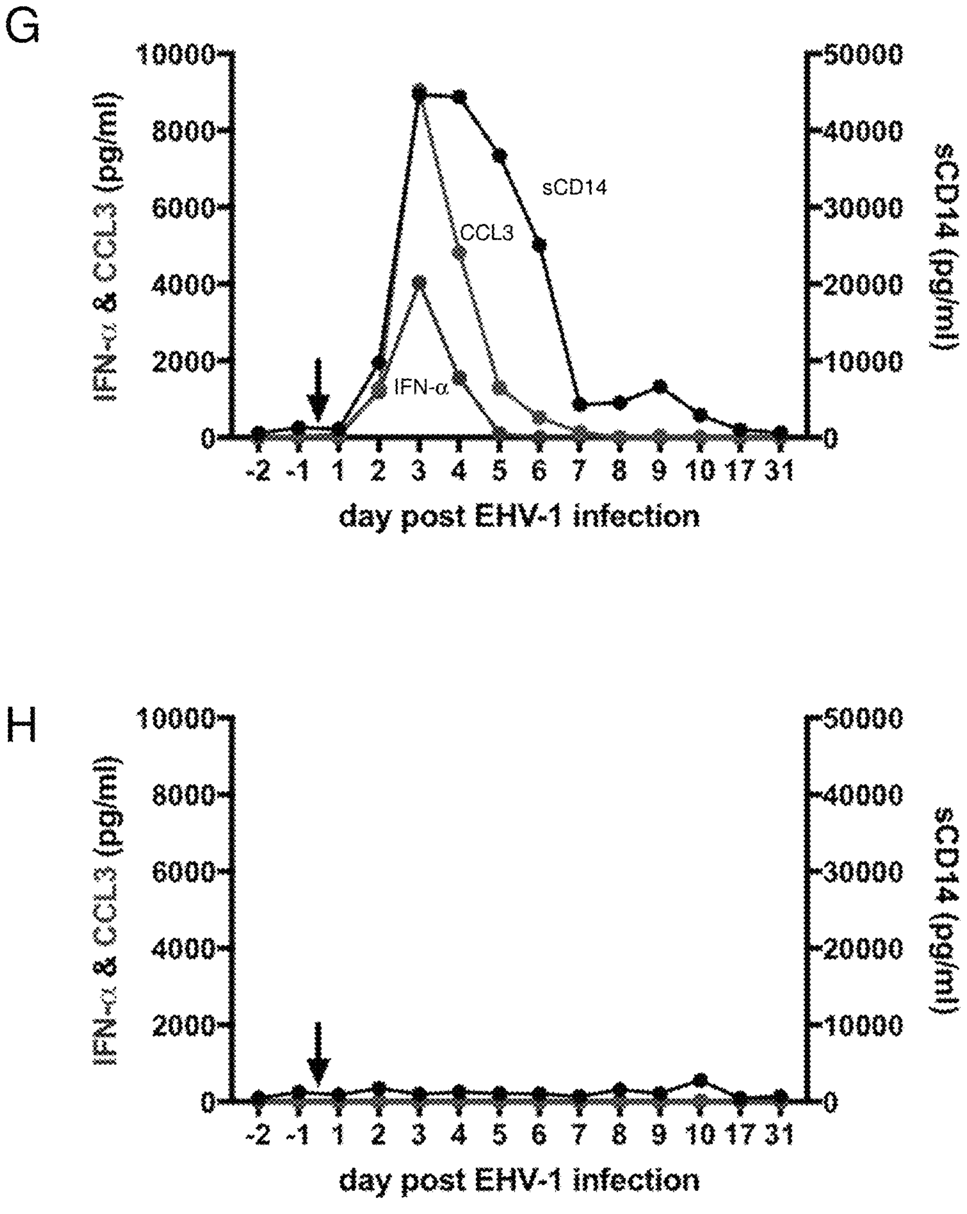

FIG. 1G summarizes the IFN-α, sCD14, and CCL3 response in the upper respiratory tract of susceptible horses. FIG. 1H summarizes the lack of IFN-α, sCD14, and CCL3 secretion in the upper respiratory tract of immune horses.

Figure 1I:
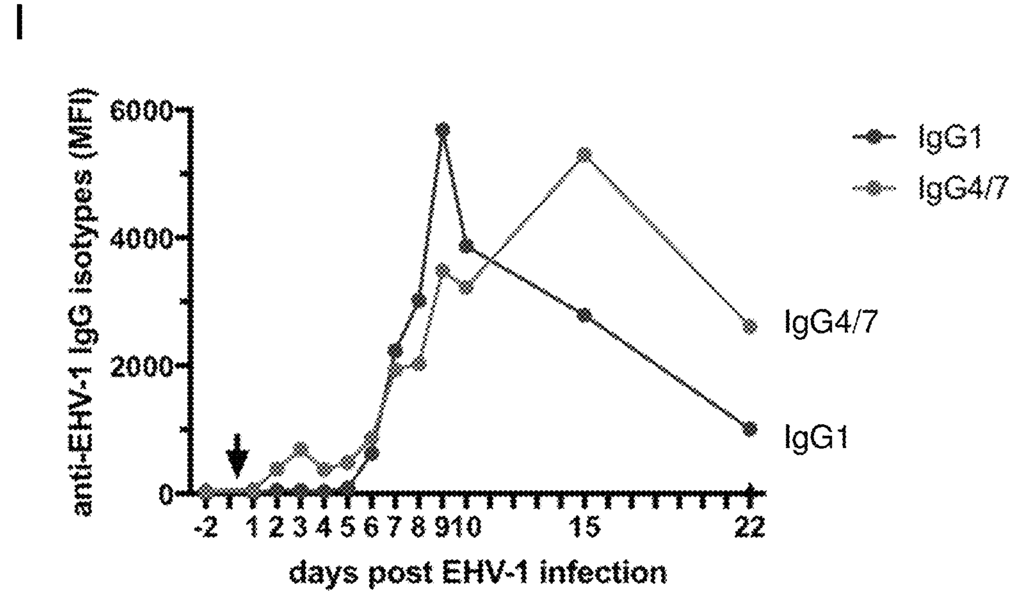
Figure 1J:
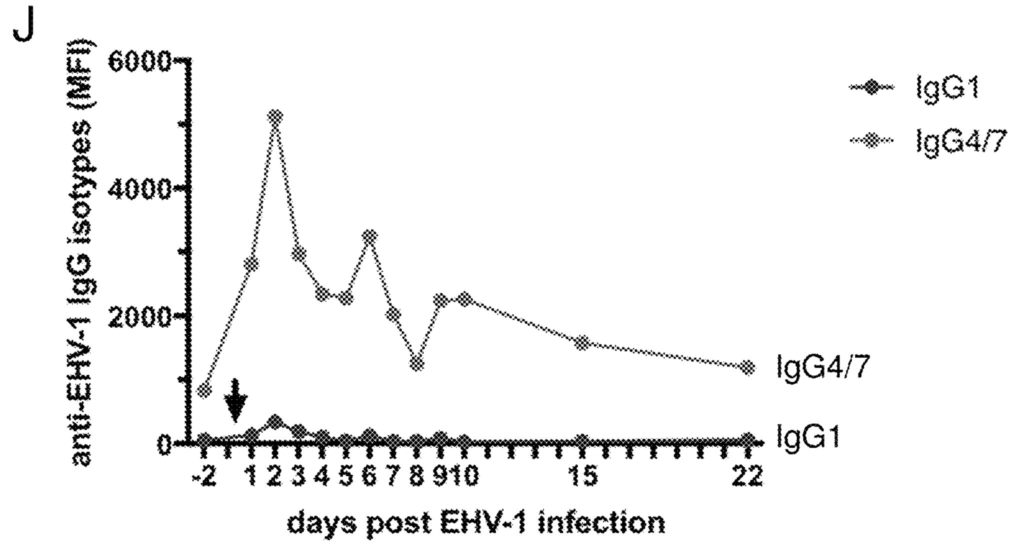

FIG. 1I shows an overlay of the anti-gC IgG1 and IgG4/7 antibody responses in the nasal secretion of EHV-1 susceptible horses. FIG. 1J shows the pre-existing intranasal anti-gC IgG4/7 response in immune horses and the rapid increase of these antibodies after EHV-1 infection in this group. IgG1 responses are low in protected horses. Consequently, these horses will always be in stage iv as long as immunity is maintained.

A specific embodiment of monitoring the stages of EHV-1 infection from nasal samples using the disclosed biomarkers is summarized in Table 1.

In the embodiment summarized in Table 1, the biomarker expression pattern is correlated with different stages of EHV-1 infection. The last three rows in Table 1 show the results of PCR-based methods for the respective EHV-1 infection stages. Especially, it is noted that PCR-based methods do not allow distinguishing between stages (i) and (iv), susceptible versus immune, in an outbreak situation. In other words, for PCR, there is no difference between susceptible horses and immune horse, as they both appear negative in a PCR-based assay. Therefore, horses already immune to EHV-1 infection are unnecessarily quarantined during an EHV-1 outbreak. PCR does also not distinguish stages (ii) and (iiia/b), early infection and shedding of high amounts of virus versus horses that are in the late stage of infection and starting to develop immunity. Horses at the end of the early and beginning of the late stage of infection are also on risk for neurologic disease and could be identified, monitored more thoroughly and treated earlier with improved biomarker analysis during outbreak situations. Therefore, the presently disclosed methods of EHV-1 detection using novel markers are superior over PCR-based methods of EHV-1 infection detection, as they allow finer classification of sick animals and immune animals.

Table 6 shows the EHV-1 neutralizing antibodies in pooled nasal secretion samples from eight immune horses (d13pi).

TABLE 6

Intranasal antibody isotypes neutralizing EHV-1

| Ig isotype | Neutralization | Neutralizing concentration (μg/ml purified antibody) |
|---|---|---|
| Total IgG | Yes | 62.5 |
| IgG1 | Yes | 62.5 |
| IgG4/7 | Yes | 125 |
| IgG3/5 | Yes | 250 |
| IgG6 | ND | Low concentration |
| IgA | No | Not neutralizing at 250 μg/ml |

Overall, secretion of IFN-α, sCD14, and CCL2 in the upper respiratory tract after EHV-1 infection correlates highly with virus shedding (Table 7). Horses secreting these inflammatory markers also shed virus and need to be quarantined.

TABLE 7

Spearman rank correlation between virus isolation (Pfu) and cytokine concentrations in nasal secretion samples of all horses (n = 15) during the first six days after infection with 1 × $10^7$ PFU EHV-1 Ab4.

| | IFN-α | | | CCL2 | | | sCD14 | | |
|---|---|---|---|---|---|---|---|---|---|
| Day pi | $r_{sp}$ | 95% CI | p-value | $r_{sp}$ | 95% CI | p-value | $r_{sp}$ | 95% CI | p-value |
| 1 | 0.6370 | 0.169-0.871 | 0.0096 | 0.4852 | −0.053-0.805 | 0.0686 | 0.1415 | −0.414-0.620 | 0.6117 |
| 2 | 0.9397 | 0.819-0.981 | <0.0001 | 0.6313 | 0.160-0.868 | 0.0138 | 0.3550 | −0.208-0.741 | 0.1935 |
| 3 | 0.9187 | 0.761-0.974 | <0.0001 | 0.7091 | 0.294-0.899 | 0.0043 | 0.7037 | 0.284-0.897 | 0.0046 |
| 4 | 0.7381 | 0.348-0.910 | 0.0059 | 0.6057 | 0.119-0.858 | 0.0187 | 0.6046 | 0.117-0.857 | 0.0189 |
| 5 | 0.2810 | −0.286-0.702 | 0.1297 | 0.3696 | −0.192-0.749 | 0.1806 | 0.5514 | 0.0379-0.835 | 0.0352 |
| 6 | 0.4422 | −0.107-0.785 | 0.2000 | −0.0621 | −0.568-0.480 | 0.8667 | 0.3093 | −0.257 to 0.717 | 0.4000 |

$r_{sp}$ = Spearman rank correlation coefficient;
95% CI = 95% confidence interval;
PFU = plaque forming units In contrast, anti-gC IgG4/7 antibodies in nasal secretion strongly correlate with protection from fever, clinical disease, virus shedding, and viremia (Table 8). For these horses quarantine can be shortened. They are not at risk of developing disease or transmitting the virus to other horses or equids.

TABLE 8

High pre-infection (d-2) intranasal anti-EHV-1 gC IgG4/7 antibodies correlate strongly with the absence of fever, clinical signs, nasal viral shedding and viremia as well as with the presence of pre-infection serum antibodies.

| | | EHV-1 gC specific antibodies in nasal secretion | | | |
|---|---|---|---|---|---|
| | | Total Ig | IgG1 | IgG4/7 | IgG3/5 |
| Fever [a] | $r_{sp}$ | −0.5997 | −0.4352 | −0.6541 | 0.07351 |
| | 95% CI | −0.8552 to −0.1097 | −0.7814 to 0.1157 | −0.8775 to −0.1972 | −0.4691 to 0.5758 |
| | p-value | 0.0203 | 0.1055 | 0.0098 | 0.7929 |
| Clinical signs [b] | $r_{sp}$ | −0.7741 | −0.5207 | −0.7813 | 0.08657 |
| | 95% CI | −0.9236 to −0.4202 | −0.821 to 0.005173 | −0.9262 to −0.4351 | −0.4588 to 0.5845 |
| | p-value | 0.0011 | 0.0486 | 0.0009 | 0.7567 |
| Viral shedding [c] | $r_{sp}$ | −0.8381 | −0.8247 | −0.8663 | 0.1049 |
| | 95% CI | −0.9465 to −0.5595 | −0.9418 to −0.529 | −0.9563 to −0.6263 | −0.444 to 0.5966 |
| | p-value | 0.0002 | 0.0003 | <0.0001 | 0.7081 |
| Viremia [d] | $r_{sp}$ | 0.6084 | 0.5545 | 0.7293 | 0 |
| | 95% CI | 0.1232 to 0.8588 | 0.04231 to 0.8359 | 0.3316 to 0.9069 | −0.5245 to 0.5245 |
| | p-value | 0.0186 | 0.0344 | 0.0030 | >0.9999 |
| Serum antibodies [e] | $r_{sp}$ | | 0.7828 | 0.8643 | 0.3303 |
| | 95% CI | 0.7112 to 0.9677 | 0.4383 to 0.9268 | 0.6215 to 0.9556 | −0.2348 to 0.7286 |
| | p-value | <0.0001 | 0.0009 | <0.0001 | 0.7770 |

[a] body temperature on d2.5 pi.; [b] clinical score on d3 pi; [c] nasal viral shedding (Pfu) on d3 pi, [d] viremia (CT value) on d5 pi; [e] corresponding pre-infection (d-2) serum antibody isotype. $r_{sp}$ = Spearman rank correlation coefficient; 95% CI = 95% confidence interval.

Figure 1K:
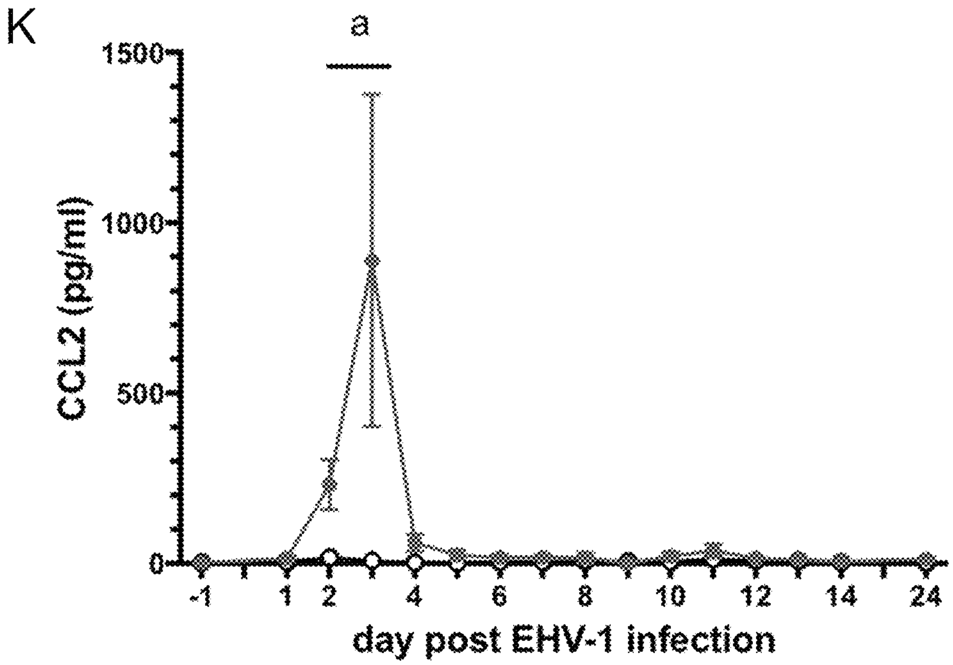

CCL3 in the disclosure can be replaced by CCL2 which shows almost the same pattern as CCL3 (FIG. 1K). However, other CCL chemokines, such as CCL5, show a different and not informative pattern.

Example 3: Previous Infection with the Neuropathogenic EHV-1 Strain Ab4 or its Deletion Mutant Ab4ΔORF1/71 (ORF1/ORF71 Gene Deletion Mutant of the EHV-1 Strain Ab4) Provided Protection from Ab4 Challenge Fifteen horses were intranasally challenged with EHV-1 Ab4. Six months prior to the challenge, horses (n=5 per group) were intranasally infected with either Ab4 (Ab4/Ab4 group), Ab4ΔORF1/71 (Ab4ΔORF1/71/Ab4 group), or not-infected (control/Ab4 group). At the time of the Ab4 challenge, horses in the control/Ab4 group were fully susceptible to EHV-1 infection. They showed a high fever at d2-3pi (day 2-3 post infection) and a secondary mild fever between d3-6pi (day 3-6 post infection) along with an increase in clinical scores between d2-4pi (day 2-4 post infection) (all $p<0.05$ to 0.0001). In contrast, horses previously infected with Ab4 or Ab4ΔORF1/71 did not develop clinical signs of disease in response to Ab4 challenge infection. This was confirmed by a lack of fever and a consistent clinical score following challenge with Ab4 in all horses in the Ab4/Ab4 and Ab4ΔORF1/71/Ab4 groups. None of the horses developed neurological signs.

Compared to the horses previously infected with Ab4 or Ab4ΔORF1/71, the control/Ab4 group shed EHV-1 in nasal secretions from d1-3pi with a significant increase on d3pi ($p=0.01$). The control/Ab4 group also developed 254 viremia with significantly higher EHV-1 DNA amounts detectable in PBMC between d4-10pi (all $p>0.05$). By comparing the clinical course of disease, nasal shedding and viremia of the control/Ab4 group with primary Ab4 infections described previously (Wimer et al., *PlosOne,* 2018, 13(11):e0206679; Schnabel et al., *BMC Vet Res.,* 2018, 14: 245), confirmed that horses in the control/Ab4 group were fully susceptible to the Ab4 challenge.

In contrast, EHV-1 was neither isolated from nasal secretions nor detected in PBMC from all horses in the Ab4/Ab4 group (5/5) and most horses in the Ab4ΔORF1/71/Ab4 group (3/5) after challenge infection with Ab4. It was concluded that 100% of horses previously infected with Ab4 263 and 60% of those infected with Ab4ΔORF1/71 (3/5) were fully protected from Ab4 challenge. The other two horses in the Ab4ΔORF1/71/Ab4 group showed no fever or clinical signs. However, low amounts of virus were isolated from their nasal secretions on d1pi or d1-3pi respectively, and one of them also was viremic on d6pi. These two horses were considered partially protected from Ab4 challenge. It was concluded that the initial infection with Ab4ΔORF1/71 induced full or partial protection against EHV-1 infection for at least 6 months post initial infection.

Although viral shedding or viremia outcomes between the Ab4/Ab4 or Ab4ΔORF1/71/Ab4 groups were not significantly different, the two partially protected horses in the latter group indicated that the ORF1/71 deletion mutant virus induced less robust protection than the parent Ab4 virus. However, initial infection with Ab4ΔORF1/71 preceding this study resulted in significantly reduced fever and nasal shedding than infection with Ab4 (Wimer et al., PlosOne, 2018, 13(11):e0206679). Based on these characteristics, the Ab4ΔORF1/71 virus can be considered as a vaccine candidate of low virulence which provides protection from EHV-1 infection for up to six months. In addition, the presently disclosed methods of EHV-1 detection using novel markers can be used to test the effectiveness of EHV-1 vaccines.

Figures 5A, 5B, 5C:
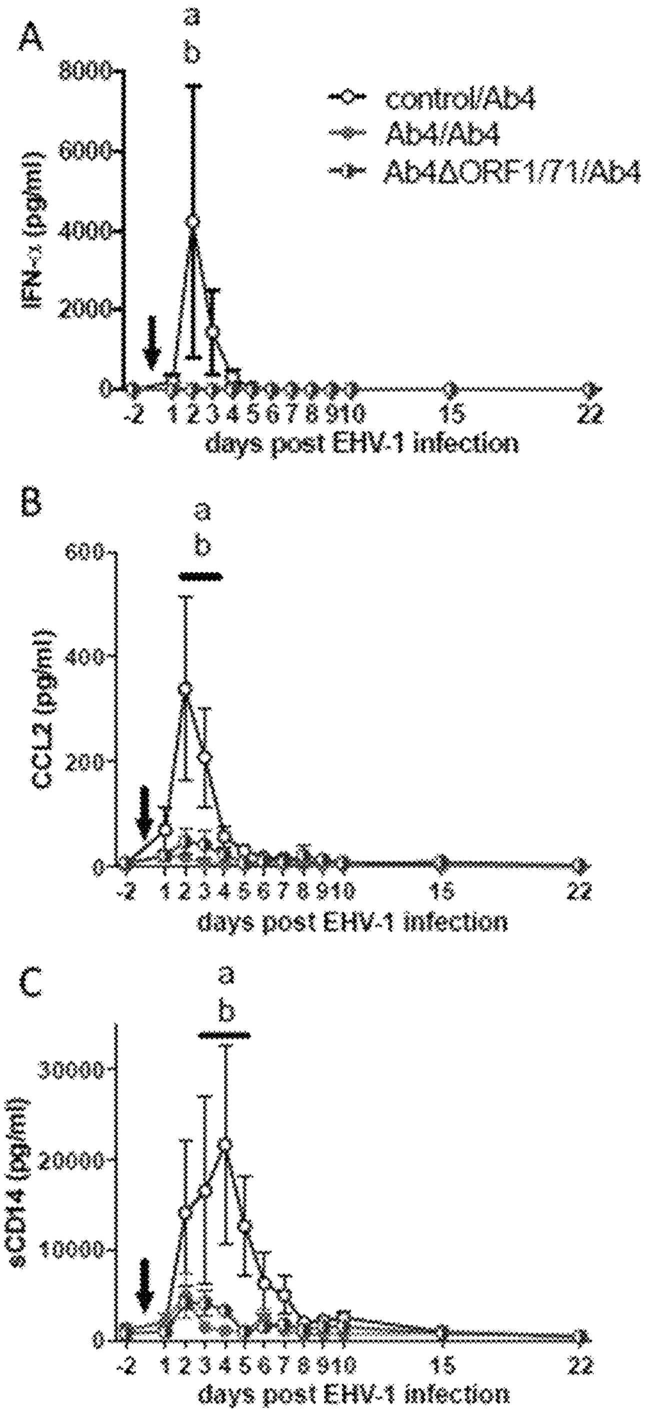
FIGS. 5A-5C. Cytokines in nasal secretion after Ab4 challenge infection of susceptible and protected horses.

Example 4: Protected Horses Lack IFN-α and Inflammatory Marker Secretion at the Local EHV-1 Infection Site On two days prior to EHV-1 infection (d-2), all 15 horses had undetectable IFN-α and CCL2, and low concentrations of sCD14 (median 0.93 ng/ml; range 0.37-2.48 ng/ml) in their nasal secretions without differences between the three groups. After Ab4 challenge, horses in the Ab4/Ab4 or Ab4ΔORF1/71/Ab4 groups were lacking IFN-α induction in their nasal secretions (FIG. 5A) and only slightly enhanced their intranasal CCL2 and sCD14 concentrations (FIGS. 5B, 5C). In contrast, IFN-α, CCL2 and sCD14 increased in the nasal secretions of the susceptible horses in the control/Ab4 group shortly after EHV-1 infection (FIGS. 5A-C). Nasal secretions of control/Ab4 horses had significantly elevated IFN-α on d2pi ($p<0.0001$), CCL2 on d2pi ($p<0.0001$) and d3pi ($p<0.01$), and sCD14 on d3-5pi ($p<0.05$ to $<0.0001$) compared to the Ab4/Ab4 or Ab4ΔORF1/71/Ab4 groups. Afterwards, all three inflammatory markers were quickly downregulated in the control/Ab4 group within the first week pi. Similar rapid increases and decreases in intranasal IFN-α and sCD14 secretion were reported after pervious experimental Ab4 infection studies of EHV-1 susceptible horses (Soboll-Hussey et al., Vet. Res., 2011; 42:23; Wimer et al., *PlosOne,* 2018, 13(11):e0206679; Schnabel et al., *BMC Vet Res.* 2018, 14: 245), while CCL2 induction after in vivo EHV-1 infection of horses is reported here for the first time. Other intranasal cytokines such as IFN-γ, IL-17A and IL-10 were of overall low concentrations despite few significant increases in their expression during the first week pi in the control/Ab4 group.

Example 5: Intranasal IFN-α and Inflammatory Marker Secretion Correlates with Nasal EHV-1 Shedding Importantly, IFN-α and CCL2 expression highly correlated with the amount of infectious EHV-1 virus isolated from nasal secretion on d1-4pi and d2-4pi, respectively, while sCD14 concentrations correlated with virus isolation between d3-5pi (Table 7). During the entire study, IFN-α was undetectable in the nasal secretion of all eight fully protected horses and also in the partially protected horse showing only one day of low viral shedding (10 PFU/ml nasal secretion). The other partially protected horse was shedding low EHV-1 amounts on d1-3pi (10-40 PFU/ml) and had low IFN-α concentrations in the nasal secretion on the same days. This confirmed that intranasal inflammatory markers, such as IFN-α, CCL2, and sCD14, represented 'danger signals' occurring simultaneously with nasal shedding of infectious EHV-1. In contrast, full protection from EHV-1 infection was characterized by the absence of nasal shedding and IFN-α secretion together with undetectable or low CCL2 and sCD14 concentrations in nasal secretions 24 hours pi and afterwards. The lack of intranasal cytokine upregulation, and especially the absence of IFN-α secretion in protected horses, strongly suggested that EHV-1 did not enter the nasal epithelium in fully protected horses. Notably, infectious Ab4 virus could also not be recovered from the nasal secretion of fully protected horses at 24 hours pi or afterwards despite the inoculation of $1\times10^7$ PFU EHV-1 Ab4 at challenge.

Figures 6A, 6B, 6C, 6D:
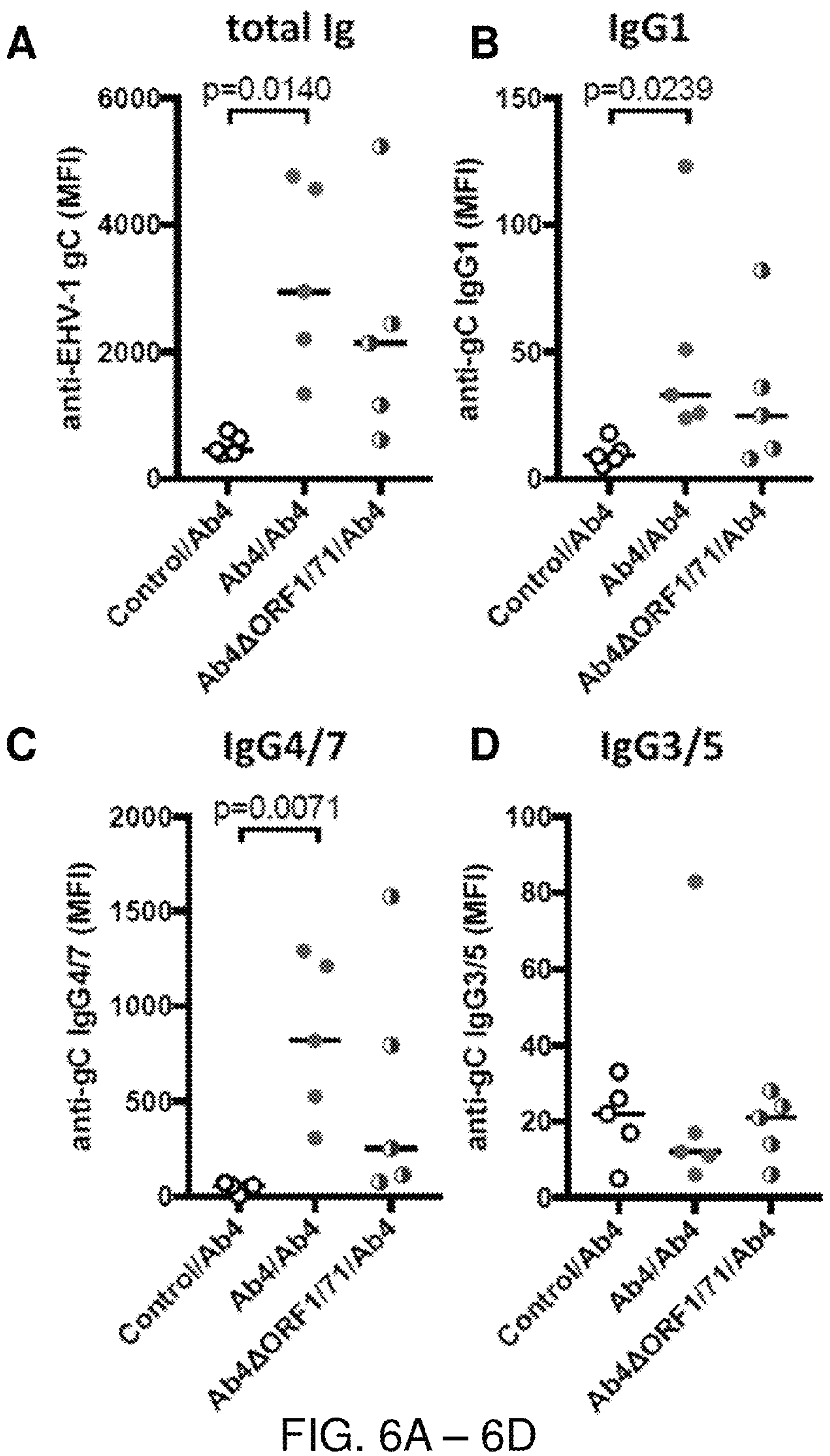

Example 6: Protective Immunity is Characterized by Preexisting EHV-1-Specific Intranasal IgG4/7 Antibodies In this approach, total antibodies and antibody isotypes against three glycoproteins of EHV-1, gB, gC and gD, were measured. Here and as shown as previously (Wimer et al., *PlosOne,* 2018, 13(11):e0206679, Schnabel et al., *BMC Vet Res,* 2018, 14: 245), antibody responses to all three EHV-1 antigens were highly similar to each other and we are therefore only showing the anti-EHV-1 gC responses. On d-2 (day 2) prior to EHV-1 infection and compared to the naïve horses in the control/Ab4 group, horses in the Ab4/Ab4 group had increased anti-gC total Ig (p=0.014) composed of some IgG1 (p=0.0239) and high amounts of IgG4/7 antibodies (p=0.0071) in their nasal secretions (FIGS. 6A-6C). All three antibody parameters were also increased for several horses in the Ab4ΔORF1/71/Ab4 although this did not reach statistical significance. Interestingly, the partially-protected horse in the Ab4ΔORF1/71/Ab4 group that showed two days of viral shedding together with low intranasal IFN-α secretion had the lowest total Ig, IgG1 and IgG4/7 values in the Ab4ΔORF1/71/Ab4 group (FIGS. 6A-6C). In contrast, pre-infection anti-gC IgG3/5 antibodies were of low magnitude in all three groups (FIG. 6D).

For all 15 horses, pre-infection total Ig and especially IgG4/7 values correlated strongly with protection from fever, clinical signs, viral shedding, and viremia. These findings strongly suggested that preexisting EHV-1-specific IgG4/7 antibodies on the mucosal surface of the upper respiratory tract can effectively and immediately neutralize EHV-1 and completely prevent viral entry into epithelial cells after experimental challenge infection with a high viral dose of neuropathogenic Ab4 virus.

Viremia is a prerequisite for EHM and abortion (Kydd et al. 1994b, Lunn et al. 2009). The absence of viremia is thus a big concern for protecting the individual horse from EHM and fatal disease and also for avoiding EHM outbreaks with all regulatory and financial consequences. Previous data have shown that serum neutralizing (SN) antibodies correlated only weakly with protection from viremia (Allen, *Am J Vet Res.,* 2008, 69: 1595-1600). The data of the present disclosure shows that anti-gC total Ig and IgG4/7 antibodies are highly correlating serum markers for prevention of viremia (Table 9). The EHV-1 gC/IL-4 based EHV-1 test provides thus a huge advantage over all existing EHV-1 assays. It is able to reliably identify horses that can be infected with EHV-1 versus those that are protected from all disease outcomes.

TABLE 9

Anti-IgC total Ig and IgG4/7 antibodies highly correlate with protection from fever, clinical disease, nasal viral shedding, and viremia in horses (n = 52) after experimental infection with $1 \times 10^7$ PRU of the neuropathogenic EHV-1 strain Ab4.

| | | | Serum antibodies (anti-gC) | |
|---|---|---|---|---|
| | | | Total Ig | IgC4/7 |
| Fever | | $r_{sp}$ | −0.7578 | −0.7711 |
| | | 95% CI | −0.8563 to −0.6062 | −0.8646 to −0.6260 |
| | | p-value | <0.0001 | <0.0001 |
| Clinical signs | | $r_{sp}$ | −0.5952 | −0.5799 |
| | | 95% CI | −0.7504 to 0.3777 | −0.7401 to −0.3576 |
| | | p-value | <0.0001 | <0.0001 |
| Viral shedding | Peak | $r_{sp}$ | −0.8883 | −0.8863 |
| | | 95% CI | −0.9357 to −0.8095 | −0.9345 to −0.8062 |
| | | p-value | <0.0001 | <0.0001 |

TABLE 9-continued

Anti-IgC total Ig and IgG4/7 antibodies highly correlate with protection from fever, clinical disease, nasal viral shedding, and viremia in horses (n = 52) after experimental infection with $1 \times 10^7$ PRU of the neuropathogenic EHV-1 strain Ab4.

| | | | Serum antibodies (anti-gC) | |
|---|---|---|---|---|
| | | | Total Ig | IgC4/7 |
| | Duration | $r_{sp}$ | −0.8611 | −0.8514 |
| | | 95% CI | −0.9195 to −0.7655 | −0.9137 to −0.7500 |
| | | p-value | <0.0001 | <0.0001 |
| Viremia | Peak | $r_{sp}$ | 0.7373 | 0.7462 |
| | | 95% CI | 0.5758 to 0.8434 | 0.5889 to 0.8490 |
| | | p-value | <0.0001 | <0.0001 |
| | Duration | $r_{sp}$ | −0.7643 | −0.7623 |
| | | 95% CI | −0.8604 to 6158 | −0.8591 to −0.6127 |
| | | p-value | <0.0001 | <0.0001 |

$r_{sp}$ = Spearman rank correlation coefficient; 95% CI = 95% confidence interval; PFU plaque forming units.

The conclusions from these analyses include the following observations:

if serum antibody values increase above 3000 MFI for anti-gC total Ig and 400 MFI for anti-gC IgG4/7, fever and clinical signs are not observed anymore after infection (equivalent of $1\times10^7$ Pfu Ab4)

as serum antibody values increase, duration of nasal viral shedding and duration of viremia decrease;

as serum antibody values increase, peak viral loads in nasal secretions decrease;

and, as serum antibody values increase, Ct values for EHV-1 PCR in the blood of the horse increase (=less EHV-1 DNA detected).

Fully protected horses do not shed any EHV-1 detectable by virus isolation and do not establish viremia as measured by PCR. Overall, this shows the suitability of using the new EHV-1 assay for the identification of fully protected horses based on serum antibody values using the two quantitative anti-EHV-1 antibody readouts of the assay.

Example 7: Interpretation of Assay Results

Immunologically, susceptible and protected horses can be distinguished by several parameters or "immune biomarkers", the most prominent of which are anti-gC total Ig and IgG4/7 in serum. The differences in antibody values between susceptible and protected horses were used to determine the protective cut-offs for the two parameters in the new EHV-1 assay. Protected horses had pre-existing antibody values for these biomarkers above the protective cut-offs shown in FIGS. 2A-2D (black dotted lines).

Table 2 lists the protective cut-off values for the assay together with the assay interpretation and resulting vaccination recommendations for anti-gC antibodies.

Figure 2A:
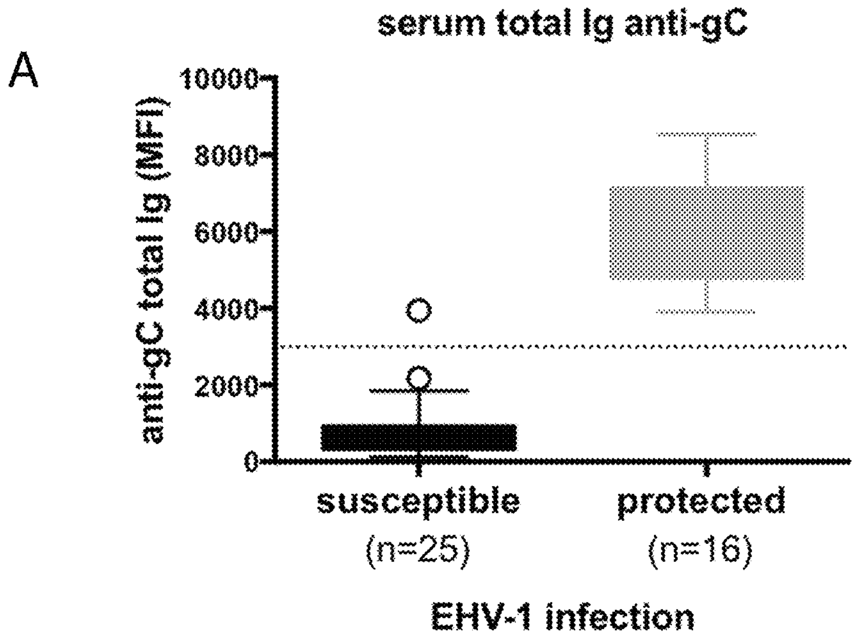
FIGS. 2A-2D. Serum analyses of horses susceptible to or protected from EHV-1 infection. (A) Total anti-gC antibodies in serum distinguish horses susceptible to or protected from EHV-1 infection. The dotted line shows the protective cut-off value (3000 MFI). Data are from 25 EHV-1 susceptible horses and 16 protected horses are shown. Data are accumulated form a total of five experimental EHV-1 infection studies using different strains of EHV-1 including neuropathogenic strains. EHV-1 susceptibility is defined as: horses infected with $1\times10^7$ Plaque Forming Units (PFU) EHV-1 developed fever (≥101.5° F.=38.6° C.), were shedding infectious EHV-1 (identified by virus isolation from nasal secretion), and developed viremia (viremia refers to presence of virus in the blood—determined in this instance in Peripheral blood mononuclear cells (PBMC) by PCR). Protected from EHV-1 infection is defined as: horses infected with $1\times10^7$ PFU EHV-1 did not develop fever (<101.5° F.=38.6° C.) or viremia (no EHV-1 DNA detected in PBMC by PCR) and did not shed virus (determined by lack of infectious virus in virus isolation). (B) Anti-gC IgG4/7 antibodies in serum distinguish horses susceptible to or protected from EHV-1 infection. The dotted line shows the protective cut-off value (400 MFI). Origin of data and definition of susceptible and protected see legend of FIG. 2A. (C) Representative distribution of serum anti-gC total Ig and IgG4/7 antibody values of 1700 horses in the US. The IgG4/7 and total Ig protective cut-off values are shown as dotted lines. Horses in the upper right quadrant are fully protected (P). Horses in the lower left quadrant are susceptible (S). Horses in the upper left and lower right quadrants are partially protected (pp). (D) Distribution of anti-gC total Ig and IgG4/7 antibodies in a group of frequently vaccinated show horses (n=52). These horses are typically vaccinated annually or twice a year. Horses are grouped based on the assay's cut-off values in S=susceptible, PP=partially protected, and P=protected individuals.
Figure 2B:
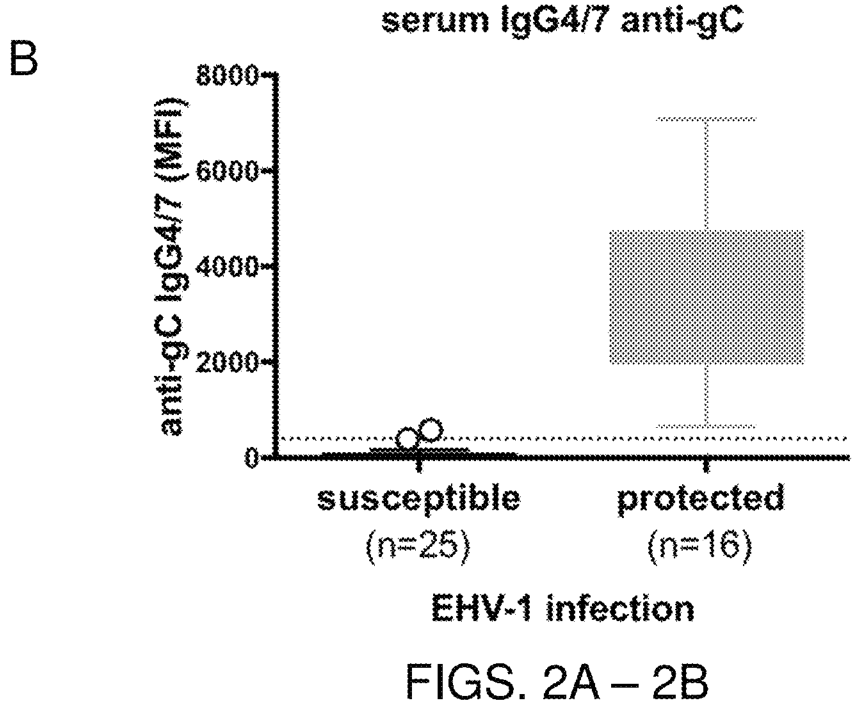

Total Ig can be composed of various Ig isotypes. IgG4/7 is the major EHV-1 neutralizing isotype in horses, while other isotypes such as IgG3, IgG5, IgM or IgA are not neutralizing EHV-1 (Table 10). IgG4/7 is also the isotype that carries long-lasting immunity against EHV-1, while IgG1 which is also neutralizing is typically short-lasting after infection or vaccination (Wagner et al., *Vaccine,* 33: 5588-5597, 2015; Schnabel, et al., *Vet Immunol Immunopathol,* 204: 28-39, 2018; Wimer et al., *PlosOne,* 13(11): e0206679, 2018). Susceptible horses can thus be reliably identified by using both markers, anti-gC total Ig and anti-gC IgG4/7. Horses with both biomarkers above the respective protective value are protected against infection and from disease (FIGS. 2A & 2B).

TABLE 10

EHV-1 neutralizing activity of antibody isotypes in the serum of protected horses.

| Antibody isotype [a] | Neutralizing activity | Concentration (μg/ml) |
|---|---|---|
| Total IgG | Yes | 500 |
| IgG1 | | 250 |
| IgG4/7 | | 125 |
| IgG3/5 | No | NA |
| IgG6 | | |
| IgA | | |

[a] Total IgG, IgG and IgA isotypes were affinity purified prior to the neutralization assay.

Susceptible horses are likely to reactivate and/or get infected with EHV-1 and can thus cause severe disease outbreaks or continue to spread EHV-1 during disease outbreaks. In contrast, protected horses will not get sick, do not shed EHV-1 and will not develop viremia. The latter is a prerequisite for developing severe and often fatal EHV-1 disease outcomes such as neurologic disease (EHM) in all horses or abortions in pregnant mares.

Figures 2C, 2D:
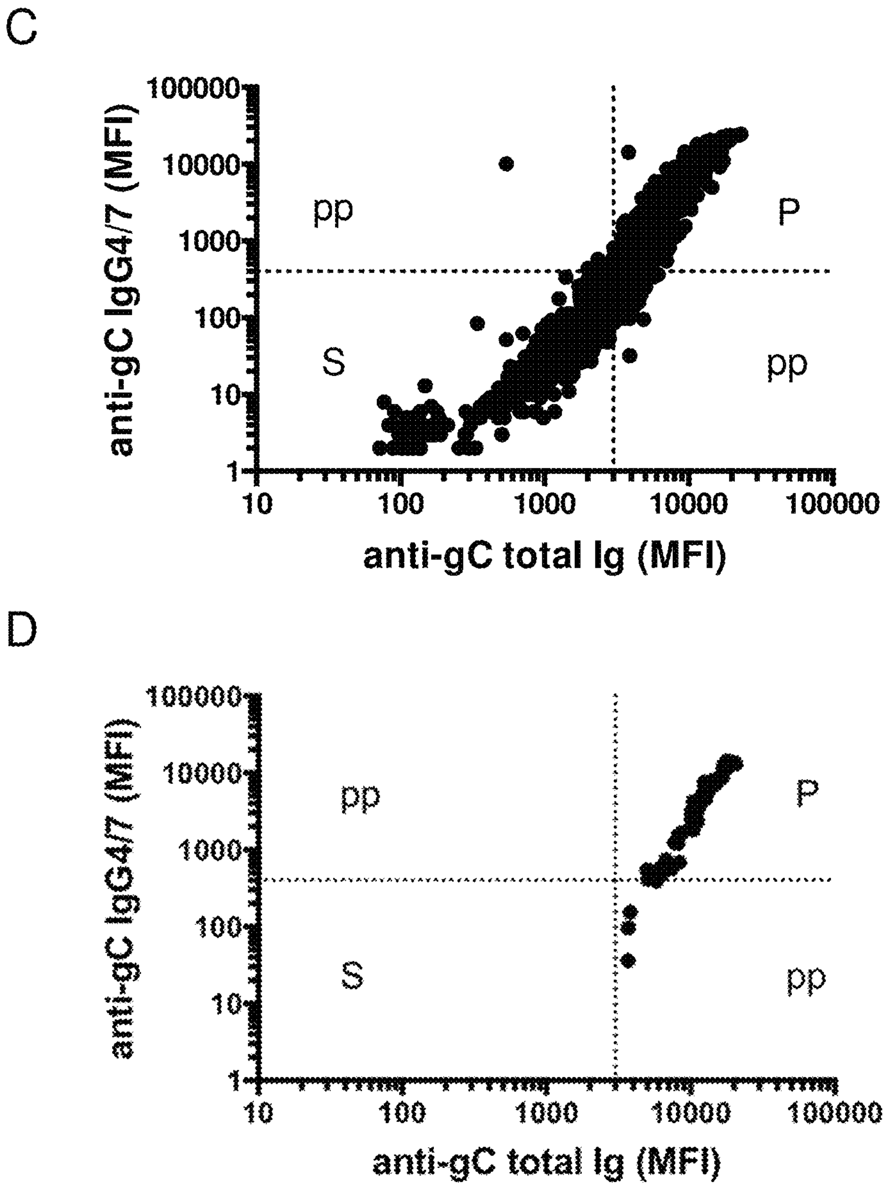
Figure 3A:
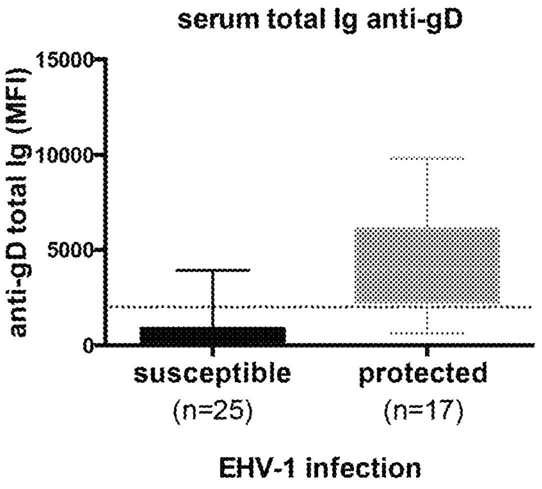
FIGS. 3A-3B. Total anti-gD antibodies (A) and anti-gD IgG4/7 (B) in serum distinguish horses susceptible to or protected from EHV-1 infection. The dotted line shows the protective cut-off values (2000 MFI; anti-gD total Ig) and (200 MFI; anti-gD IgG4/7). Data are from 25 EHV-1 susceptible horses and 17 protected horses are shown. Data are accumulated form a total of five experimental EHV-1 infection studies using different strains of EHV-1 including neuropathogenic strains. EHV-1 susceptibility is defined as: horses infected with $1\times10^7$ PFU EHV-1 developed fever (≥101.5° F.=38.6° C.), were shedding infectious EHV-1 (identified by virus isolation from nasal secretion), and developed viremia (determined in PBMC by PCR). Protected from EHV-1 infection is defined as: horses infected with $1\times10^7$ PFU EHV-1 did not develop fever (<101.5° F.=38.6° C.) or viremia (no EHV-1 DNA detected in PBMC by PCR) and did not shed virus (determined by lack of infectious virus in virus isolation).
Figure 3B:
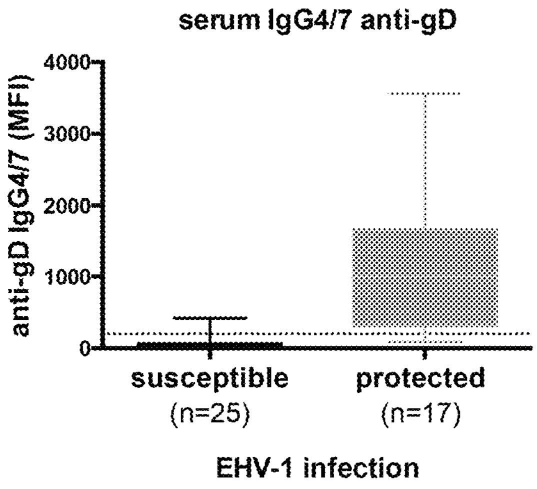
Figures 4A, 4B:
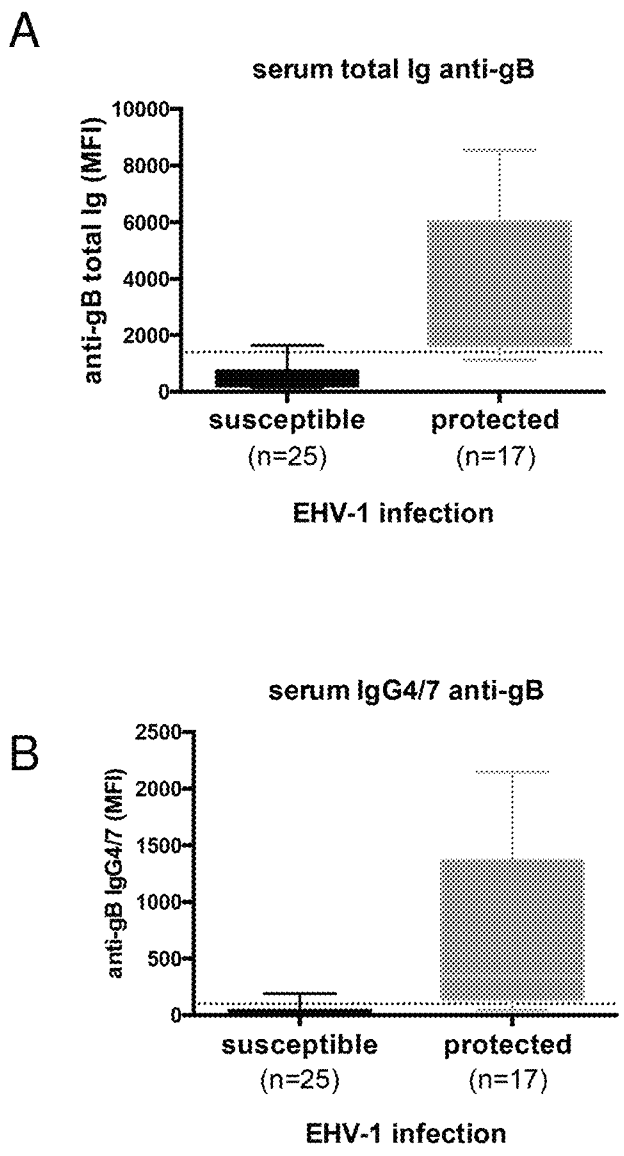
FIGS. 4A-4B. Total anti-gB antibodies (A) and anti-gB IgG4/7 (B) in serum distinguish horses susceptible to or protected from EHV-1 infection. The dotted line shows the protective cut-off values (1400 MFI; anti-gB total Ig) and (100 MFI; anti-gB IgG4/7). Data are from 25 EHV-1 susceptible horses and 17 protected horses are shown. Data are accumulated form a total of five experimental EHV-1 infection studies using different strains of EHV-1 including neuropathogenic strains. EHV-1 susceptibility is defined as: horses infected with $1\times10^7$ PFU EHV-1 developed fever (>101.5° F.=38.6° C.), were shedding infectious EHV-1 (identified by virus isolation from nasal secretion), and developed viremia (determined in PBMC by PCR). Protected from EHV-1 infection is defined as: horses infected with $1\times10^7$ PFU EHV-1 did not develop fever (<101.5° F.=38.6° C.) or viremia (no EHV-1 DNA detected in PBMC by PCR) and did not shed virus (determined by lack of infectious virus in virus isolation).

A representative set of equine serum samples (n=1700) showed that approximately 35% of the equine population is currently susceptible to EHV-1 infection (FIG. 2C). The horses in this approach included many young horses and horses that are not regularly transported. Another set of representative adult horses that are traveling (n=500) showed that about 13% of these horses are susceptible for EHV-1 infection. A group of show horses (n=52) that are vaccinated annually or twice a year was analyzed with the assay indicating that most of these horses were protected. However, a few horses did not mount anti-EHV-1 antibodies high enough to be considered fully protected (FIG. 2D). These horses are still at risk on getting infected with EHV-1, transmit the virus and/or develop viremia and potentially EHM.

The high percentage of susceptible horses exists despite widely used EHV vaccination and is a result of either not vaccinating horses or short-lasting vaccine antibodies in combination with low immune responsiveness of individual horses. Susceptible horses and those that do not mount protective antibody values despite frequent vaccination are on risk of getting infected and developing severe fatal neurologic disease.

What is claimed is:

1. A method comprising:

(a) providing an intranasal sample from a horse in a herd of horses;

(b) detecting in said sample equine herpes virus type 1 (EHV-1) specific immunoglobulin G1 (IgG1) and EHV-1 specific immunoglobulin G4/7 (IgG4/7), wherein the EHV-1 specific IgG1 and the EHV-1 specific IgG4/7 are both directed against a glycoprotein C (gC) of EHV-1, and wherein the detection of the EHV-1 specific IgG4/7 and the EHV-1 specific IgG1 is achieved by a multiplex assay based on use of a gC/IL-4 fusion protein;

(c) determining whether the horse is susceptible or immune to EHV-1 infection, or is undergoing an infection, wherein the horse is susceptible to EHV-1 infection or is at an early stage of EHV-1 infection if the levels of the EHV-1 specific IgG1 and the EHV-1 specific IgG4/7 are both below respective threshold levels;

wherein the horse is at a late stage of EHV-1 infection if the levels of the EHV-1 specific IgG1 and the EHV-1 specific IgG4/7 are both above respective threshold levels; and wherein the horse is immune to EHV-1 infection, if the level of the EHV-1 specific IgG1 is below a respective threshold level, the level of EHV-1 specific IgG4/7 is above a respective threshold level, and the ratio of the level of the EHV-1 specific IgG4/7 versus the level of the EHV-1 specific IgG1 is more than 10; and (d) quarantining the horse away from other horses in the herd during an EHV-1 outbreak if the horse is susceptible to EHV-1 infection or at an early or late stage of EHV-1 infection, wherein the horse is quarantined for at least 14 days if the horse is susceptible to EHV-1 infection or is at an early stage infection, and the horse is quarantined for not more than 14 days if the horse is at a late stage of EHV-1 infection; and not quarantining the horse if the horse is immune to EHV-1 infection.

2. The method of claim 1, comprising, when the levels of the EHV-1 specific IgG1 and the EHV-1 specific IgG4/7 are below respective threshold levels, further detecting in the sample interferon α (IFN-α), chemokine (C-C motif) ligand 3 (CCL3), and soluble cluster of differentiation 14 (sCD14), and determining that the horse is at an early stage of EHV-1 infection when the level of at least one of IFN-α, CCL3 and sCD14 is above a respective threshold level.

3. The method of claim 1, comprising, when the levels of the EHV-1 specific IgG1 and the EHV-1 specific IgG4/7 are below respective threshold levels, further detecting in the sample interferon α (IFN-α), chemokine (C-C motif) ligand 2 (CCL2), and soluble cluster of differentiation 14 (sCD14), and determining that the horse is at an early stage of EHV-1 infection when the level of at least one of IFN-α, CCL2 and sCD14 is above a respective threshold level.

4. The method of claim 1, wherein the threshold level for the EHV-1 specific IgG1 is 1000 median fluorescent intensities (MFI), and the threshold level for the EHV-1 specific IgG4/7 is 1000 median fluorescent intensities (MFI).

5. The method of claim 1, wherein the horse has been recently determined to be susceptible to EHV-1 infection or at an early stage of EHV-1 infection.

6. The method of claim 1, wherein the early stage of EHV-1 infection comprises days between day 2 and day 7 post infection, and wherein the late stage EHV-1 infection comprises days between day 8 and day 21 post infection.

7. A method comprising, (a) providing an intranasal sample from a horse in a herd of horses;

(b) detecting in said sample EHV-1 specific IgG1, EHV-1 specific IgG4/7, IFN-α, CCL3, and sCD14, wherein the EHV-1 specific IgG1 and the EHV-1 specific IgG4/7 are both directed against a glycoprotein C (gC) of EHV-1, wherein the detection of the EHV-1 specific IgG4/7 and the EHV-1 specific IgG1 is achieved by a multiplex assay based on use of a gC/IL-4 fusion protein;

(c) determining that the horse is susceptible to EHV-1 infection, when the levels of the EHV-1 specific IgG1, the EHV-1 specific IgG4/7, IFN-α, CCL3 and sCD14 are all below respective threshold levels;

determining that the horse is at an early stage of EHV-1 infection, when the level of at least one of IFN-α, CCL3 and sCD14 is above a respective threshold level and the levels of the EHV-1 specific IgG1 and the EHV-1 specific IgG4/7 are both below respective threshold levels;

determining that the horse is at a late stage of EHV-1 infection, when the levels of the EHV-1 specific IgG1 and the EHV-1 specific IgG4/7 are both above respective threshold levels, and the levels of IFN-α, CCL3 and sCD14 are all below respective threshold levels; and determining that the horse is immune to EHV-1 infection, when the level of the EHV-1 specific IgG4/7 is above a respective threshold level and the ratio of the level of the EHV-1 specific IgG4/7 versus the level of the EHV-1 specific IgG1 is more than 10, and the levels of EHV-1 specific IgG1, IFN-α, CCL3 and sCD14 are all below respective threshold levels; and (d) quarantining the horse away from other horses in the herd during an EHV-1 outbreak if the horse is susceptible to EHV-1 infection, at an early stage of EHV-1 infection, or at a late stage of EHV-1 infection, wherein the horse is quarantined for at least 14 days if the horse is susceptible to EHV-1 infection or at an early stage of EHV-1 infection, and the horse is quarantined for not more than 14 days if the horse is at a late stage of EHV-1 infection; and not quarantining the horse during the EHV-1 outbreak if the horse is immune to EHV-1 infection.

8. A method comprising, (a) providing an intranasal sample from a horse in a herd of horses;

(b) detecting in said sample EHV-1 specific IgG1, EHV-1 specific IgG4/7, IFN-α, CCL2, and sCD14, wherein the EHV-1 specific IgG1 and the EHV-1 specific IgG4/7 are both directed against a glycoprotein C (gC) of EHV-1, wherein the detection of the EHV-1 specific IgG4/7 and the EHV-1 specific IgG1 is achieved by a multiplex assay based on use of a gC/IL-4 fusion protein;

(c) determining that the horse is susceptible to EHV-1 infection, when the levels of the EHV-1 specific IgG1, the EHV-1 specific IgG4/7, IFN-α, CCL2 and sCD14 are all below respective threshold levels;

determining that the horse is at an early stage of EHV-1 infection, when the level of at least one of IFN-α, CCL2 and sCD14 is above a respective threshold level and the levels of the EHV-1 specific IgG1 and the EHV-1 specific IgG4/7 are both below respective threshold levels;

determining that the horse is at a late stage of EHV-1 infection, when the levels of the EHV-1 specific IgG1 and the EHV-1 specific IgG4/7 are both above respective threshold levels, and the levels of IFN-α, CCL2 and sCD14 are all below respective threshold levels; and determining that the horse is immune to EHV-1 infection, when the level of the EHV-1 specific IgG4/7 is above a respective threshold level and the ratio of the level of the EHV-1 specific IgG4/7 versus the level of the EHV-1 specific IgG1 is more than 10, and the levels of EHV-1 specific IgG1, IFN-α, CCL2 and sCD14 are all below respective threshold levels; and (d) quarantining the horse away from other horses in the herd during an EHV-1 outbreak if the horse is susceptible to EHV-1 infection, at an early stage of EHV-1 infection, or at a late stage of EHV-1 infection, wherein the horse is quarantined for at least 14 days if the horse is susceptible to EHV-1 infection or at an early stage of EHV-1 infection, and the horse is quarantined for not more than 14 days if the horse is at a late stage of EHV-1 infection; and not quarantining a horse during the EHV-1 outbreak if the horse is immune to EHV-1 infection.

9. The method of claim 7, wherein the threshold level for the EHV-1 gC specific IgG1 is 1000 median fluorescent intensities (MFI), the threshold level for the EHV-1 gC specific IgG4/7 is 1000 median fluorescent intensities (MFI), the threshold level for IFN-α is 100 pg/ml, the threshold level for CCL3 is 100 pg/ml, and the threshold level for sCD14 is 2000 pg/ml.

10. The method of claim 7, wherein the threshold level for the EHV-1 gC specific IgG1 is 1000 median fluorescent intensities (MFI), the threshold level for the EHV-1 gC specific IgG4/7 is 1000 median fluorescent intensities (MFI), the threshold level for IFN-α is 100 pg/ml, the threshold level for CCL2 is 100 pg/ml, and the threshold level for sCD14 is 2000 pg/ml.

11. The method of claim 7, wherein the early stage of EHV-1 infection comprises days between day 2 and day 7 post infection, and wherein the late stage EHV-1 infection comprises days between day 8 and day 21 post infection.

12. The method of claim 7, wherein the detection of the EHV-1 specific IgG4/7 and the EHV-1 specific IgG1 are achieved by assay comprising a cytokine/EHV-1 glycoprotein fusion protein.

13. The method of claim 8, wherein the, threshold level for the EHV-1 gC specific IgG1 is 1000 median fluorescent intensities (MFI), the threshold level for the EHV-1 gC specific IgG4/7 is 1000 median fluorescent intensities (MFI), the threshold level for IFN-α is 100 pg/ml, the threshold level for CCL3 is 100 pg/ml, and the threshold level for sCD14 is 2000 pg/ml.

14. The method of claim 8, wherein the, threshold level for the EHV-1 gC specific IgG1 is 1000 median fluorescent intensities (MFI), the threshold level for the EHV-1 gC specific IgG4/7 is 1000 median fluorescent intensities (MFI), the threshold level for IFN-α is 100 pg/ml, the threshold level for CCL2 is 100 pg/ml, and the threshold level for sCD14 is 2000 pg/ml.

15. The method of claim 8, wherein the early stage of EHV-1 infection comprises days between day 2 and day 7 post infection, and wherein the late stage EHV-1 infection comprises days between day 8 and day 21 post infection.

* * * * *